(12) United States Patent
Sweeney

(10) Patent No.: US 7,938,848 B2
(45) Date of Patent: May 10, 2011

(54) SPINAL FIXATION SYSTEM

(75) Inventor: Patrick J. Sweeney, Flossmoor, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 0 days.

(21) Appl. No.: 10/864,673

(22) Filed: Jun. 9, 2004

(65) Prior Publication Data
US 2005/0277923 A1 Dec. 15, 2005

(51) Int. Cl.
*A61B 17/70* (2006.01)
(52) U.S. Cl. ........................................................ 606/246
(58) Field of Classification Search ................ 606/61, 606/72, 73, 99, 104
See application file for complete search history.

(56) References Cited

U.S. PATENT DOCUMENTS

| | | | |
|---|---|---|---|
| 2,414,882 A | 1/1947 | Longfellow | |
| 3,289,290 A * | 12/1966 | Sandor | 29/432 |
| 4,399,814 A | 8/1983 | Pratt, Jr. et al. | |
| 4,648,388 A * | 3/1987 | Steffee | 606/61 |
| 4,653,489 A | 3/1987 | Tronzo | |
| 4,790,297 A | 12/1988 | Luque | |
| 4,805,602 A | 2/1989 | Puno et al. | |
| 4,863,472 A | 9/1989 | Tormala et al. | |
| 5,047,029 A | 9/1991 | Aebi et al. | |
| 5,092,893 A | 3/1992 | Smith | |
| 5,098,435 A * | 3/1992 | Stednitz et al. | 606/73 |
| 5,129,899 A | 7/1992 | Small et al. | |
| 5,261,909 A | 11/1993 | Sutterlin et al. | |
| 5,350,380 A * | 9/1994 | Goble et al. | 606/80 |
| 5,352,226 A | 10/1994 | Lin | |
| 5,423,819 A * | 6/1995 | Small et al. | 606/232 |
| 5,449,257 A | 9/1995 | Giannuzzi | |
| 5,545,163 A | 8/1996 | Miller | |
| 5,562,661 A | 10/1996 | Yoshimi et al. | |
| 5,569,252 A * | 10/1996 | Justin et al. | 606/73 |
| 5,582,612 A * | 12/1996 | Lin | 606/61 |
| 5,584,833 A | 12/1996 | Fournet-Fayard et al. | |
| 5,611,800 A | 3/1997 | Davis et al. | |
| 5,616,142 A | 4/1997 | Yuan et al. | |
| 5,643,262 A | 7/1997 | Metz-Stavenhagen et al. | |
| 5,649,931 A * | 7/1997 | Bryant et al. | 606/104 |
| 5,667,513 A * | 9/1997 | Torrie et al. | 606/104 |
| 5,688,275 A | 11/1997 | Koros et al. | |
| 5,885,285 A | 3/1999 | Simonson | |
| 5,938,663 A | 8/1999 | Petreto | |

(Continued)

FOREIGN PATENT DOCUMENTS
WO    WO 02/36026    5/2002

(Continued)

OTHER PUBLICATIONS

Lamendola, Mark, How to Use Belleville Washers Correctly, Dec. 1, 1997, EC&M.*
Chen, Pei-Yu et al., "Closed Reduction With Intramedullary Fixation for Midclavicular Fractures," Orthopedics journal, May 2004, pp. 459-462, vol. 27, No. 5.
International Search Report and Written Opinion for Application No. PCT/US05/20157, date of mailing Jan. 6, 2006, 9 pages.

(Continued)

*Primary Examiner* — Anu Ramana
(74) *Attorney, Agent, or Firm* — Foley & Lardner LLP

(57) ABSTRACT

A spinal fixation system includes a pedicle screw having a passage extending along a longitudinal axis of the screw. The passage has a proximal opening at a proximal end of the screw and a distal opening at a distal end of the screw. A drill extends through the passage, a first end of the drill extending out the distal opening of the passage.

15 Claims, 27 Drawing Sheets

U.S. PATENT DOCUMENTS

| | | | |
|---|---|---|---|
| 5,947,967 | A | 9/1999 | Barker |
| 5,951,558 | A | 9/1999 | Fiz |
| 5,976,135 | A | 11/1999 | Sherman et al. |
| 6,001,098 | A | 12/1999 | Metz-Stavenhagen et al. |
| 6,030,388 | A | 2/2000 | Yoshimi et al. |
| 6,033,406 | A | 3/2000 | Mathews |
| 6,045,555 | A | 4/2000 | Smith et al. |
| 6,048,343 | A | 4/2000 | Mathis et al. |
| 6,059,785 | A | 5/2000 | Schavan et al. |
| 6,063,089 | A | 5/2000 | Errico et al. |
| 6,063,090 | A * | 5/2000 | Schlapfer ............ 606/61 |
| 6,096,060 | A * | 8/2000 | Fitts et al. ............ 606/232 |
| 6,111,164 | A | 8/2000 | Rainey et al. |
| 6,123,706 | A | 9/2000 | Lange |
| 6,139,549 | A * | 10/2000 | Keller ............ 606/61 |
| 6,159,210 | A | 12/2000 | Voor |
| 6,179,838 | B1 * | 1/2001 | Fiz ............ 606/61 |
| 6,183,473 | B1 | 2/2001 | Ashman |
| 6,193,721 | B1 | 2/2001 | Michelson |
| 6,210,376 | B1 | 4/2001 | Grayson |
| 6,210,413 | B1 | 4/2001 | Justis et al. |
| 6,224,602 | B1 | 5/2001 | Hayes |
| 6,228,085 | B1 | 5/2001 | Theken et al. |
| 6,231,575 | B1 * | 5/2001 | Krag ............ 606/61 |
| 6,248,104 | B1 | 6/2001 | Chopin et al. |
| 6,248,105 | B1 | 6/2001 | Schlapfer et al. |
| 6,248,107 | B1 | 6/2001 | Foley et al. |
| 6,254,602 | B1 * | 7/2001 | Justis ............ 606/61 |
| 6,258,089 | B1 | 7/2001 | Campbell et al. |
| 6,273,889 | B1 | 8/2001 | Richelsoph |
| 6,306,136 | B1 | 10/2001 | Baccelli |
| 6,315,779 | B1 * | 11/2001 | Morrison et al. ............ 606/69 |
| 6,317,957 | B1 * | 11/2001 | Gregor et al. ............ 29/429 |
| 6,355,039 | B1 * | 3/2002 | Troussel et al. ............ 606/61 |
| 6,364,881 | B1 | 4/2002 | Apgar et al. |
| 6,371,957 | B1 * | 4/2002 | Amrein et al. ............ 606/61 |
| 6,379,357 | B1 | 4/2002 | Bernstein et al. |
| 6,398,783 | B1 | 6/2002 | Michelson |
| 6,402,749 | B1 | 6/2002 | Ashman |
| 6,402,756 | B1 | 6/2002 | Ralph et al. |
| 6,413,259 | B1 | 7/2002 | Lyons et al. |
| 6,428,542 | B1 | 8/2002 | Michelson |
| 6,454,769 | B2 | 9/2002 | Wagner et al. |
| 6,471,703 | B1 | 10/2002 | Ashman |
| 6,503,250 | B2 | 1/2003 | Paul |
| 6,533,786 | B1 | 3/2003 | Needham et al. |
| 6,582,436 | B2 | 6/2003 | Schlapfer et al. |
| 6,599,290 | B2 | 7/2003 | Bailey et al. |
| 6,602,257 | B1 | 8/2003 | Thramann |
| 6,613,050 | B1 | 9/2003 | Wagner et al. |
| 6,616,665 | B2 | 9/2003 | Grafton et al. |
| 6,620,163 | B1 | 9/2003 | Michelson |
| 6,626,906 | B1 | 9/2003 | Young |
| 6,641,583 | B2 * | 11/2003 | Shluzas et al. ............ 606/61 |
| 6,641,586 | B2 | 11/2003 | Varieur |
| 6,648,887 | B2 | 11/2003 | Ashman |
| 6,648,894 | B2 | 11/2003 | Abdelgany et al. |
| 6,663,642 | B2 | 12/2003 | Beyar et al. |
| 6,668,688 | B2 | 12/2003 | Zhao et al. |
| 6,669,700 | B1 | 12/2003 | Farris et al. |
| 6,676,661 | B1 | 1/2004 | Martin Benlloch et al. |
| 6,685,705 | B1 | 2/2004 | Taylor |
| 6,695,846 | B2 | 2/2004 | Richelsoph et al. |
| 6,706,045 | B2 | 3/2004 | Lin et al. |
| 6,723,100 | B2 | 4/2004 | Biedermann et al. |
| 6,755,835 | B2 | 6/2004 | Schultheiss et al. |
| 6,786,907 | B2 | 9/2004 | Lange |
| 6,827,722 | B1 | 12/2004 | Schoenefeld |
| 6,832,999 | B2 | 12/2004 | Ueyama et al. |
| 6,835,196 | B2 * | 12/2004 | Biedermann et al. ............ 606/61 |
| 6,858,030 | B2 | 2/2005 | Martin et al. |
| 6,893,444 | B2 | 5/2005 | Orbay |
| 6,899,714 | B2 * | 5/2005 | Vaughan ............ 606/86 A |
| 6,949,100 | B1 | 9/2005 | Venturini |
| 6,951,561 | B2 | 10/2005 | Warren et al. |
| 7,604,643 | B2 | 10/2009 | Ciccone et al. |
| 2001/0041894 | A1 | 11/2001 | Campbell et al. |
| 2002/0045896 | A1 | 4/2002 | Michelson |
| 2002/0045899 | A1 | 4/2002 | Errico et al. |
| 2002/0111630 | A1 | 8/2002 | Ralph et al. |
| 2002/0120273 | A1 | 8/2002 | Needham et al. |
| 2002/0128655 | A1 | 9/2002 | Michelson |
| 2002/0143332 | A1 | 10/2002 | Lin et al. |
| 2002/0147450 | A1 | 10/2002 | LeHuec et al. |
| 2002/0151899 | A1 | 10/2002 | Bailey et al. |
| 2002/0169450 | A1 | 11/2002 | Lange |
| 2002/0183748 | A1 | 12/2002 | Martin et al. |
| 2002/0183754 | A1 | 12/2002 | Michelson |
| 2002/0183755 | A1 | 12/2002 | Michelson |
| 2002/0183756 | A1 | 12/2002 | Michelson |
| 2002/0183757 | A1 | 12/2002 | Michelson |
| 2002/0188296 | A1 | 12/2002 | Michelson |
| 2003/0000350 | A1 | 1/2003 | Zhao et al. |
| 2003/0023240 | A1 | 1/2003 | Amrein et al. |
| 2003/0023242 | A1 | 1/2003 | Harrington, Jr. |
| 2003/0040749 | A1 | 2/2003 | Grabowski et al. |
| 2003/0045878 | A1 | 3/2003 | Petit et al. |
| 2003/0060828 | A1 | 3/2003 | Michelson |
| 2003/0073997 | A1 | 4/2003 | Doubler et al. |
| 2003/0083658 | A1 | 5/2003 | Hawkes et al. |
| 2003/0105460 | A1 | 6/2003 | Crandall et al. |
| 2003/0105462 | A1 | 6/2003 | Haider |
| 2003/0149431 | A1 | 8/2003 | Varieur |
| 2003/0149432 | A1 | 8/2003 | Frigg et al. |
| 2003/0171751 | A1 | 9/2003 | Ritland |
| 2003/0191473 | A1 | 10/2003 | Taylor |
| 2003/0208202 | A1 | 11/2003 | Falahee |
| 2004/0010253 | A1 | 1/2004 | Morrison |
| 2004/0034356 | A1 | 2/2004 | LeHuec et al. |
| 2004/0068319 | A1 | 4/2004 | Cordaro |
| 2004/0087951 | A1 | 5/2004 | Khalili |
| 2004/0092930 | A1 | 5/2004 | Petit et al. |
| 2004/0102773 | A1 | 5/2004 | Morrison et al. |
| 2004/0102780 | A1 | 5/2004 | West, Jr. |
| 2004/0106924 | A1 | 6/2004 | Ralph et al. |
| 2004/0122426 | A1 | 6/2004 | Michelson |
| 2004/0127896 | A1 | 7/2004 | Lombardo et al. |
| 2004/0127897 | A1 | 7/2004 | Freid et al. |
| 2004/0127899 | A1 | 7/2004 | Konieczynski et al. |
| 2004/0147928 | A1 | 7/2004 | Landry et al. |
| 2004/0181226 | A1 | 9/2004 | Michelson |
| 2004/0181229 | A1 | 9/2004 | Michelson |
| 2004/0186476 | A1 | 9/2004 | Michelson |
| 2004/0204712 | A1 | 10/2004 | Kolb et al. |
| 2004/0215190 | A1 * | 10/2004 | Nguyen et al. ............ 606/61 |
| 2004/0220571 | A1 | 11/2004 | Assaker et al. |
| 2004/0220572 | A1 | 11/2004 | Michelson |
| 2004/0236335 | A1 | 11/2004 | Michelson |
| 2004/0243139 | A1 | 12/2004 | Lewis et al. |
| 2005/0027297 | A1 | 2/2005 | Michelson |
| 2005/0027298 | A1 | 2/2005 | Michelson |
| 2005/0033298 | A1 | 2/2005 | Hawkes et al. |
| 2005/0043732 | A1 | 2/2005 | Dalton |
| 2005/0059971 | A1 | 3/2005 | Michelson |
| 2005/0075699 | A1 | 4/2005 | Olson et al. |
| 2005/0113830 | A1 | 5/2005 | Rezach et al. |
| 2005/0113833 | A1 | 5/2005 | Davison |
| 2005/0149026 | A1 | 7/2005 | Butler et al. |
| 2006/0079903 | A1 | 4/2006 | Wong |
| 2006/0089647 | A1 | 4/2006 | Culbert et al. |
| 2006/0149234 | A1 | 7/2006 | de Coninck |
| 2006/0195096 | A1 | 8/2006 | Lee et al. |
| 2006/0224241 | A1 | 10/2006 | Butler et al. |
| 2007/0118122 | A1 | 5/2007 | Butler et al. |
| 2007/0173833 | A1 | 7/2007 | Butler et al. |

FOREIGN PATENT DOCUMENTS

| | | | |
|---|---|---|---|
| WO | WO 03/028538 A2 | 4/2003 | |

OTHER PUBLICATIONS

Office Action for U.S. Appl. No. 11/071,604, dated Oct. 17, 2007, 14 pages.

"The Trio® Spinal System," printed Feb. 9, 2005, 2 pages.

* cited by examiner

SPINAL FIXATION SYSTEM

FIELD OF THE INVENTION

The present invention relates to instrumentation and methods used in the performance of spinal fusion procedures. In particular, the present invention relates to a spinal fixation system and related surgical methods.

BACKGROUND OF THE INVENTION

The spinal column is comprised of twenty-six interlocking vertebrae. These vertebrae are separated by disks. The spine provides load-bearing support for one-half of the body's mass and it protects the nerves of the spinal column. The disks provide shock absorption and facilitate the bending of the spine.

The combination of the vertebrae and disks at each vertebral segment allows for motion of the spine, in particular, flexing, rotation, and extension. The motion and support functions of the spine, in combination with the many interlocking parts and nerve roots associated with the spinal column can result in back pain due to various reasons. Such back pain may result from the degeneration of disks due to age, disease, or injury. Further, vertebral bodies may be compromised due to disease or defect, such as a tumor, or injury, such as fracture.

Spinal fusion or fixation surgery is one way to treat back pain. Further, spinal fusion or fixation may be used to correct an abnormal curvature of the spine or stabilize the spine due to injury or disease affecting one or more disks or vertebrae. In a spinal fusion procedure, two or more adjacent vertebrae in the spine are fused together. The fusion is typically accomplished by the utilization of spinal instrumentation including pedicle screws and associated rods or plates used to mechanically fix the vertebrae together. Pedicle screws are typically used in spinal fusion surgery because the pedicle serves as a strong mechanical attachment point to the spine. Bone graft material may be utilized to aid in the creation of bone structure between the fused vertebrae to create a single bone.

Spinal fixation components vary depending on the system being utilized but typically include pedicle screws that are inserted through the pedicle and into the vertebral body. The pedicle screws are attached to one another by a linking device, such as a rod or plate, that extends vertically along the row of pedicle screws that are inserted. Several coupling systems are known in the art that are used for coupling the pedicle screws to the linking device, which is oriented parallel to the spinal column. Typically two columns of pedicle screws and linking devices are used, one on each side of the spinal column. After installation, the two linking devices may be attached to one another to provide additional stabilization of that portion of the spine. As an alternative or in addition to pedicle screws, spinal hooks may be used, each spinal hook being coupled to a vertebra via a portion of the vertebral arch.

Because of anatomical variations, the pedicle screws that are fixed to one another in a spinal fusion procedure may not be in longitudinal alignment with one another. Accordingly, spinal fixation systems, whether utilizing a rod or a plate, strive to allow some variability in the placement of the pedicle screws while still accomplishing the goal of fixation with a single rod or plate along the pedicle screws.

One challenge associated with the design of a spinal fixation system is the connection between the pedicle screws and the linking device. Ideally, the number of components involved should be minimized, especially the number of components that must be threaded together (such as nuts and rods) in order to ease the assembly process and minimize the overall time of the surgical procedure.

There is also a need for a spinal fixation system that may be utilized with a minimally invasive surgical approach, such as one that utilizes smaller access apertures or ports rather than a large incision along the entire portion of the spine being treated. A spinal fixation system that addresses the needs for a minimally invasive approach may also address the desire to utilize bone graft material along the fixation site to enhance bony in-growth.

Further, there is a need for a spinal fixation system that not only utilizes fewer components but that requires fewer steps for assembly onto the spine, thus shortening the overall time of the surgical procedure.

It would be desirable to provide a system and/or method that provides one or more of these or other advantageous features or addresses one or more of the above-identified needs. Other features and advantages will be made apparent from the present specification. The teachings disclosed extend to those embodiments that fall within the scope of the appended claims, regardless of whether they accomplish one or more of the above-identified needs.

SUMMARY OF THE INVENTION

The invention relates to a spinal fixation system having a pedicle screw with a longitudinal axis and a passage in the pedicle screw extending along the longitudinal axis, the passage having a proximal opening at a proximal end of the screw and a distal opening at a distal end of the screw. A drill extends through the passage, a first end of the drill extending out the distal opening.

The invention further relates to a spinal fixation system having a pedicle screw and a linking device configured to connect the pedicle screw to at least one additional pedicle screw. A coupling mechanism is configured to be received on the pedicle screw, the coupling mechanism having a collet and a fastening device, the fastening device connecting both the linking device and the collet to the pedicle screw.

The invention further relates to a spinal fixation system having a pedicle screw with a shaft portion and a threaded portion configured to be screwed into a bone. A linking device is configured to connect the pedicle screw to additional pedicle screws. A coupling mechanism is configured to connect the pedicle screw to the linking device. A bone graft implant has a reservoir configured to contain a bone graft material, and an aperture in the reservoir sized to receive the shaft portion to couple the bone graft implant to the pedicle screw.

The invention further relates to a mechanism for coupling a pedicle screw to a fixation rod in a spinal fixation system. A first plate has a first aperture adapted to receive a pedicle screw and a second plate is hinged to the first plate, the second plate having a second aperture adapted to receive the pedicle screw. A hook extends from the first plate and is configured to receive a fixation rod. An engagement arm extends from the second plate, the engagement arm configured to press against the fixation rod to lock the fixation rod into the hook.

The invention further relates to a spinal instrumentation kit having a pedicle screw with a passage extending along a longitudinal axis, the passage having a proximal opening at a proximal end of the screw and a distal opening at a distal end of the screw. The kit further contains a drill adapted to extend through the passage.

The invention further relates to a method for connecting a pedicle screw to a bone. The method includes the steps of opening an aperture in a patient to permit access to a bone, providing a pedicle screw having a passage extending along a longitudinal axis of the screw, the passage having a keyed portion, a proximal opening at a proximal end of the screw, and a distal opening at a distal end of the screw. The method further includes the steps of providing a drill having a shaft, a cutting tip, and a keyed segment configured to interlock with the keyed portion, inserting the drill into the passage such that the cutting tip protrudes from the distal opening and the keyed segment interlocks with the keyed portion, and rotating the drill and screw to simultaneously drill a pilot hole and screw the pedicle screw into the bone. The method further includes the step of removing the drill from the pedicle screw without also removing the pedicle screw from the bone.

The invention further relates to a method for attaching a pedicle screw to a bone and coupling a linking device to the pedicle screw. The method includes the steps of opening an aperture in a patient to permit access to a bone, providing a pedicle screw having a passage extending along a longitudinal axis of the screw, the passage having a proximal opening at a proximal end of the screw and a distal opening at a distal end of the screw, providing a drill having a shaft and a cutting tip, and inserting the drill into the passage such that the cutting tip protrudes from the distal opening and the shaft protrudes from the proximal opening. The method further includes the steps of providing a linking device and a coupling mechanism configured to connect the linking device to the pedicle screw, the coupling mechanism having at least one component having an aperture configured to receive the pedicle screw, placing the component over the shaft of the drill, sliding the component onto the pedicle screw, and coupling the linking device to the pedicle screw.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION OF PREFERRED EMBODIMENTS

Figure 1:
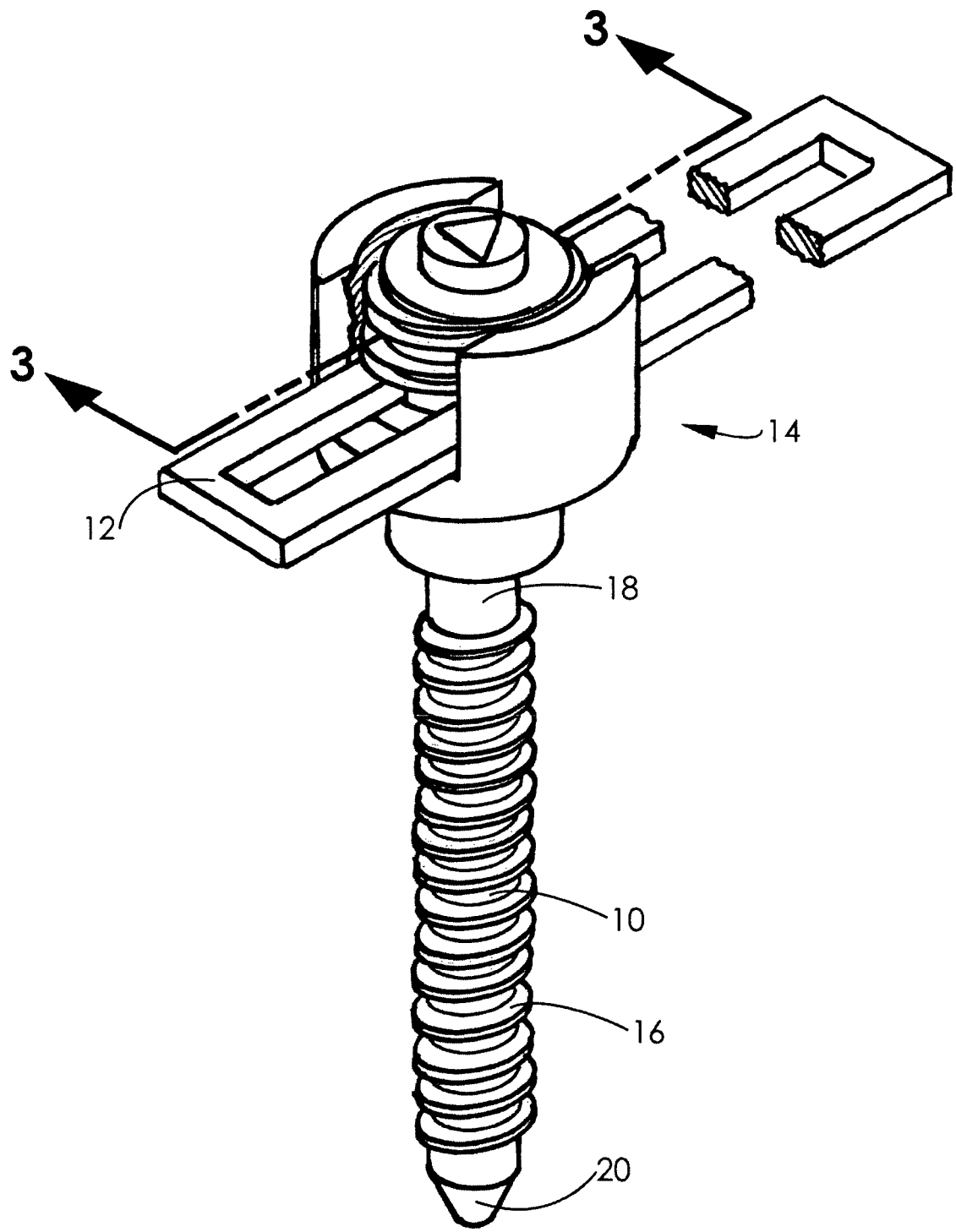
FIG. 1 is a perspective view of a spinal fixation system.

Referring to FIG. 1, in an exemplary embodiment of the invention, a spinal fixation system includes a bone anchoring element or bone screw, shown as pedicle screw 10. The pedicle screw 10 is coupled to a fixation element or linking device, shown as fixation plate 12, via a coupling mechanism 14. In use, the pedicle screw 10 may be inserted through a pedicle and into a vertebra and linked to other pedicle screws by the fixation plate 12. The length of the fixation plate 12 is chosen to accommodate the total distance between the pedicle screws that are linked together.

Figure 2:
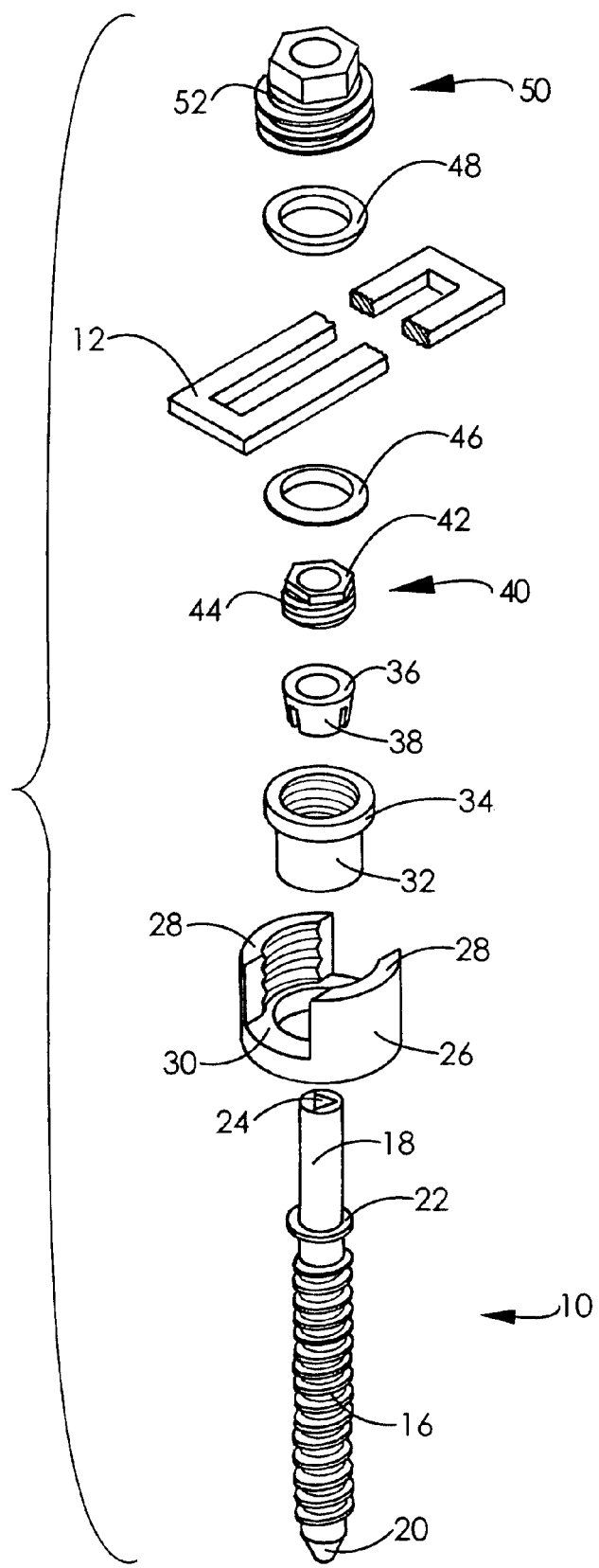
FIG. 2 is an exploded perspective view of the spinal fixation system of FIG. 1.

Referring to FIG. 2, the pedicle screw 10 includes a threaded portion 16 and a non-threaded upper portion, shown as post 18. A tip 20 may be configured to be self-drilling and a shoulder or flange 22 may extend from the screw 10 between the post 18 and threaded portion 16. At the top of the post 18, an engagement mechanism for a screwdriver or drill, shown as recess 24, may be utilized. A receiver 26 includes a pair of wall portions 28 that together form a U-shaped receiver sized to receive fixation plate 12. The internal side of wall portions 28 may be threaded to engage with other instrumentation. The wall portions 28 extend upwardly from base 30.

Further referring to FIG. 2, collar 32 has a threaded interior portion and a shoulder 34 that is sized to rest upon base 30. A collet 36 includes a number of compressible arms 38 intended to engage with pedicle screw 10 upon assembly. A lower set screw 40 has a head 42 that may be configured to be grasped by a tool, such as the hex-head configuration shown in FIG. 2. A threaded portion 44 is configured to engage with the internal threads of the collar 32 during assembly. A pair of retaining rings 46, 48 engage either side of fixation plate 12, the lower retaining ring 46 resting upon collar 32 and the upper retaining ring 48 compressed between the fixation plate 12 and an upper set screw 50. The upper set screw 50 has a threaded portion 52 intended to engage with the threaded interior side of wall portions 28 of the receiver 26 upon assembly. The upper set screw 50 may have a head configuration designed to be engaged by a wrench or other tightening tool.

Figure 3:
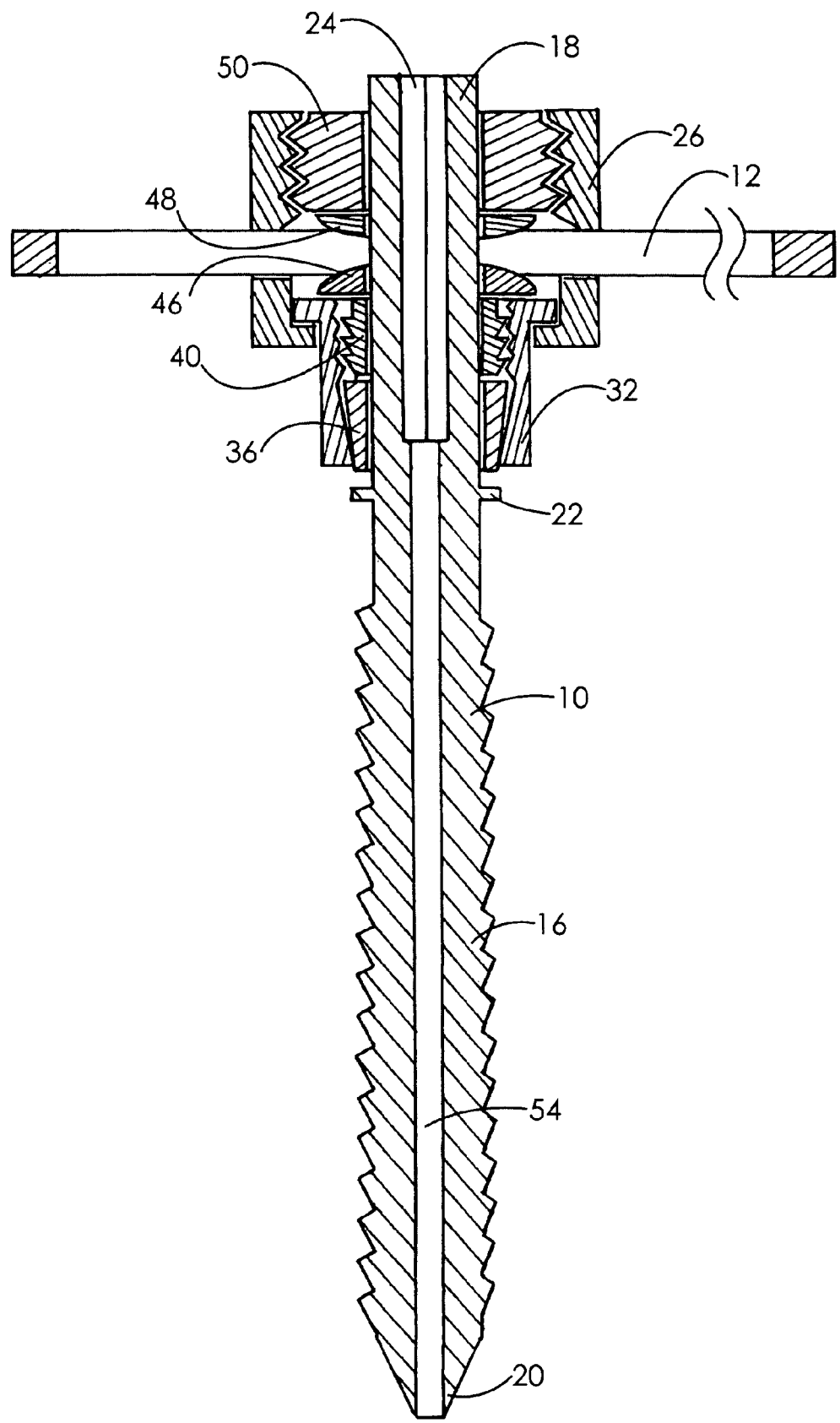
FIG. 3 is a sectional view of the spinal fixation system of FIG. 1 taken generally along line 3-3 of FIG. 1.

Referring to FIG. 3, while an upper portion of the interior of collar 32 is threaded to engage with lower set screw 40, the lower portion is not threaded but has a tapered interior portion having a more narrow diameter at the bottom of the collar 32. During assembly of the fixation system, the collar 32 is dropped into the receiver 26, the shoulder 34 resting upon the base 30. Note that each of the components forming the coupling mechanism has an interior channel or aperture configured to allow the components to be placed upon and encircle the post 18. The collet 36 is placed into collar 32, the outer diameter of the collet 36 being greater along a portion of the longitudinal axis of collet 36 than the interior diameter of collar 32, as shown in FIG. 3. The lower set screw 40 may then be threaded into collar 32, thus engaging collet 36 and pushing collet 36 downward through the collar 32 until the compressible arms 38 are forced to grip and be secured to post 18. Engagement of the post 18 by the collet 36 locks the collet 36 and the other components of the coupling mechanism into place relative to the pedicle screw 10 for fixation to the fixation plate 12.

Note that the collet 36 may be locked onto post 18 at any position along the longitudinal axis of post 18, affording flexibility in the placement of the coupling mechanism components. In other pedicle screw embodiments, the collet may engage with the threaded portion of the pedicle screw. The flexibility in placement of the collet is important due to the variability in placement of the pedicle screw 10 depending on the anatomy of the patient's spine. Once the receiver 26, collar 32, and collet 36 are locked into place onto pedicle screw 10, the fixation plate 12 may be linked to the pedicle screw 10 by placing retainer rings 46, 48 over the post 18 on either side of the fixation plate 12 and locking the fixation plate 12 into place by threading upper set screw 50 into receiver 26 to complete the assembly.

Further referring to FIG. 3, the recess 24 extends into the pedicle screw 10 to create a keyed portion of a passage 54 that extends the length of the pedicle screw 10. The keyed portion may serve as an engagement point for a driver as discussed above.

Figure 4:
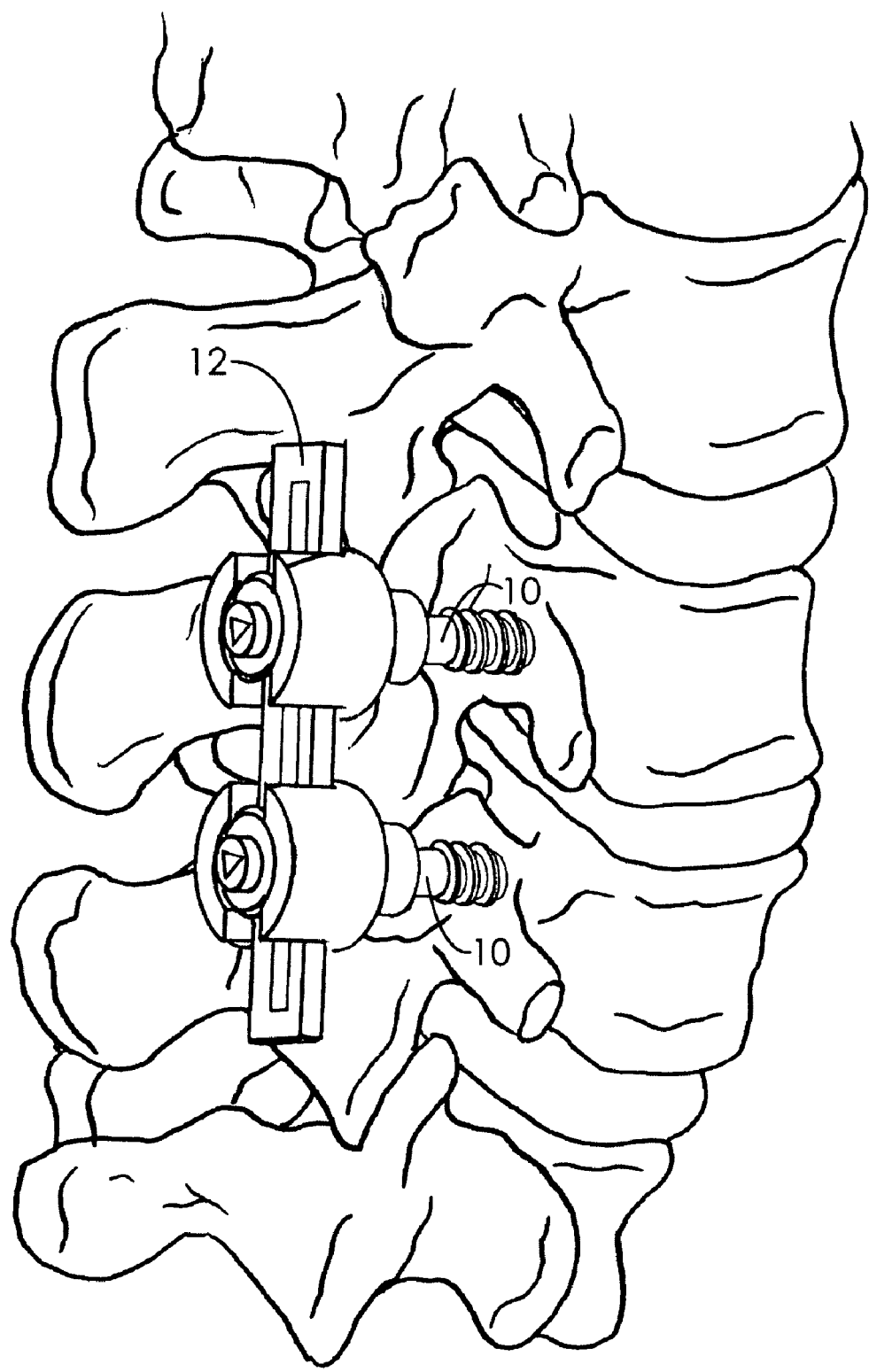
FIG. 4 is a perspective view of the spinal fixation system of FIG. 1 connected to a spine.

Referring to FIG. 4, the embodiment of the spinal fixation system shown in FIGS. 1-3 is shown installed into a patient's spine. In practice, the pedicle screws 10 may be individually installed prior to the installation of the fixation plate 12 across the multiple pedicle screws 10. Note that the fixation plate 12 is centered upon the line of pedicle screws 10 as opposed to the offset configuration seen with other fixation system embodiments.

Figure 5:
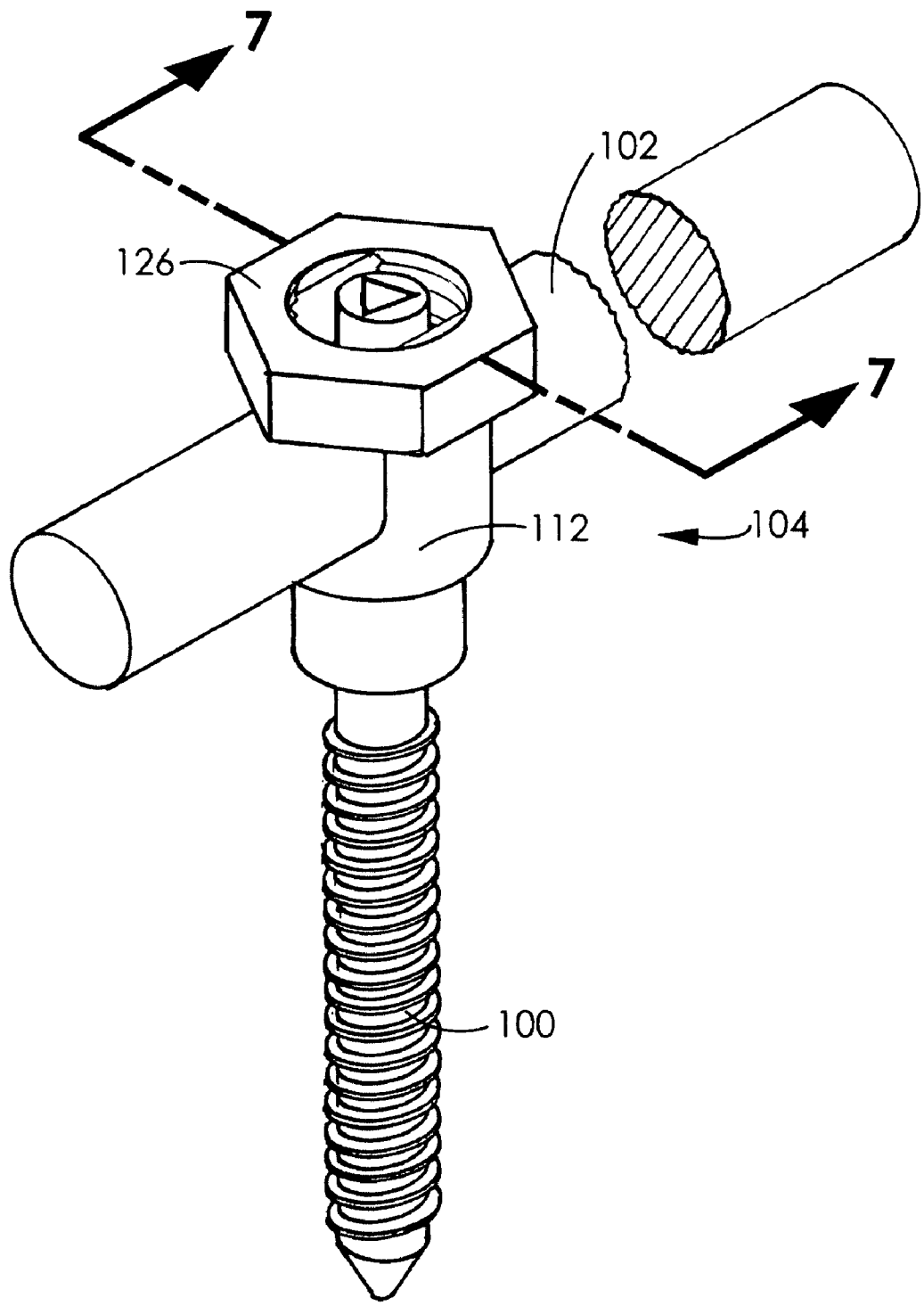
FIG. 5 is a perspective view of a spinal fixation system.

Referring to FIG. 5, a fixation system in accordance with another embodiment of the invention is shown and includes a bone coupling element or bone screw, shown as pedicle screw 100, a linking device, shown as fixation rod 102, and a coupling mechanism (generally shown as coupling mechanism 104) used to connect the pedicle screw 100 and fixation rod 102 together. The fixation rod 102 provides similar functionality to the fixation plate 12.

Figure 6:
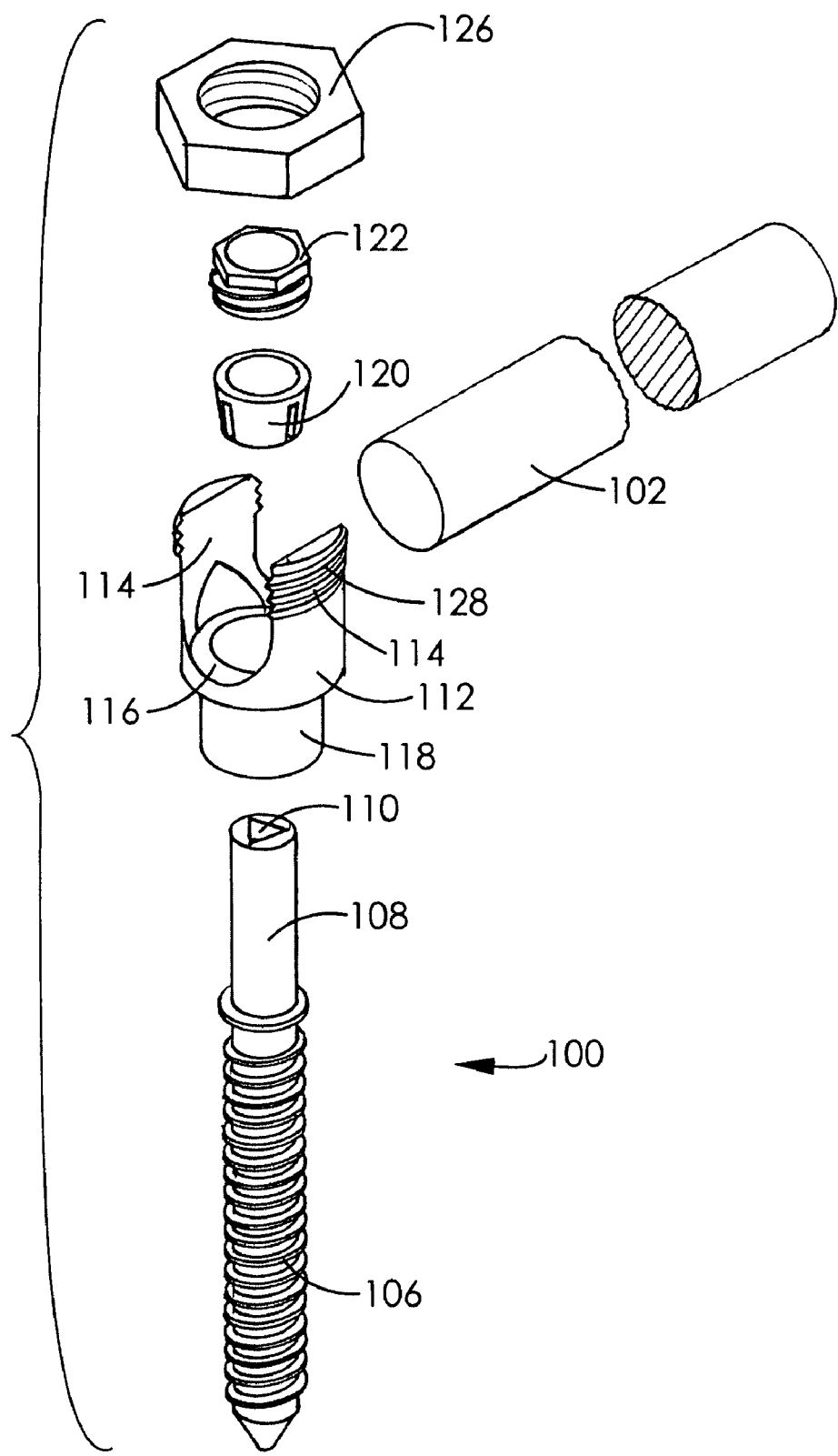
FIG. 6 is an exploded perspective view of the spinal fixation system of FIG. 5.

Referring to FIG. 6, pedicle screw 100 includes a threaded portion 106 and a non-threaded post 108. A recess 110 is provided at the top of pedicle screw 100 in order to provide an engagement point for a drill or screwdriver. In this embodiment as with other embodiments described herein, the triangle-shaped recess is exemplary only and may take various forms such as a slot or a hexagonal recess depending on the type of tool utilized for turning the pedicle screw. A receiver 112 includes a pair of wall portions 114 extending upwardly from base 116. A collar 118 is integrally formed as part of the receiver 112. The U-shaped configuration of the upwardly extending wall portions 114 and base 116 is suited to receive and be attached to fixation rod 102. A collet 120 is sized to fit into the collar 118 and be pressed downward by a set screw 122, the set screw 122 having a threaded portion 124 such that it may be screwed into the collar 118. A nut 126 is sized to be connected to a threaded portion 128 of the receiver 112.

Figure 7:
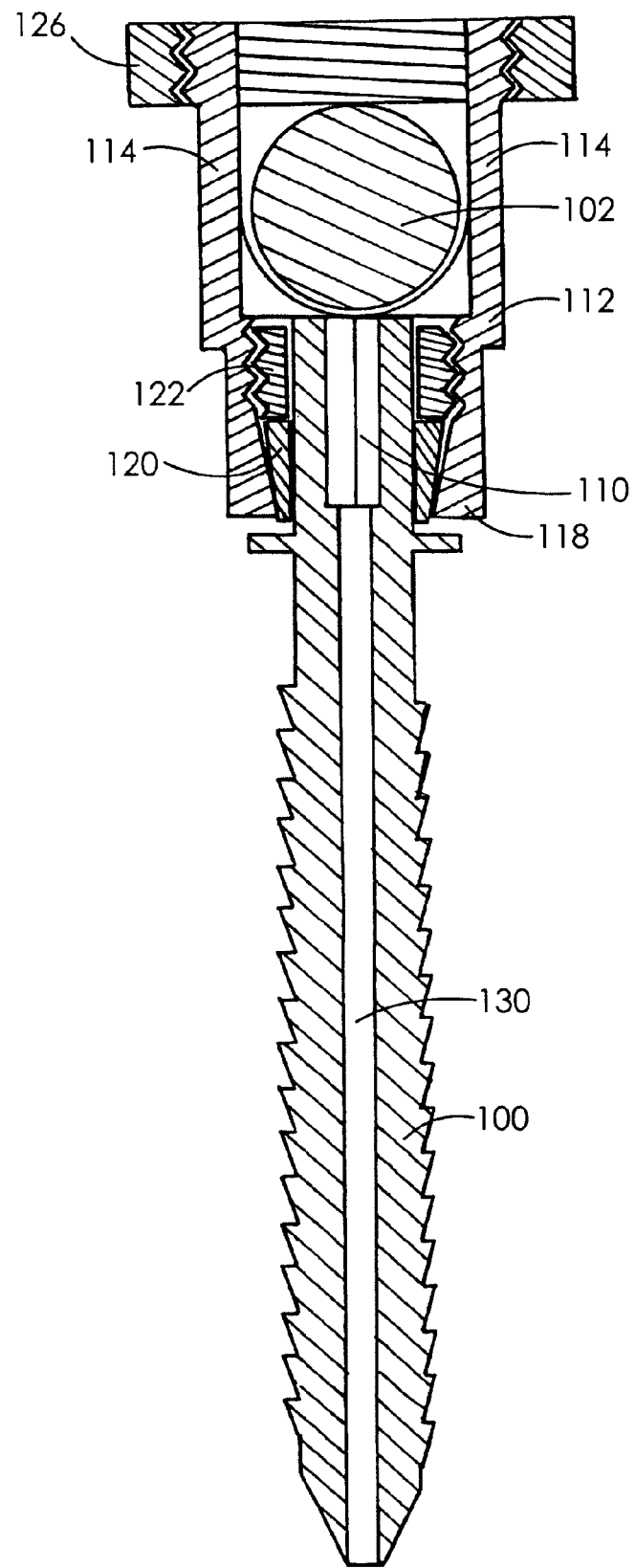
FIG. 7 is a sectional view of the spinal fixation system of FIG. 5 taken generally along line 7-7 of FIG. 5.

Referring to FIG. 7, the fixation rod 102 is attached to the pedicle screw 100 by the various components of the coupling mechanism. In particular, the receiver 112 is first placed upon the post 108, followed by insertion of the collet 120 and the set screw 122 into the receiver 112 and collar 118. Tightening the set screw 122 forces the collet 120 downward through the narrowing passageway of the collar 118 such that the compressible arms of the collet 120 are forced inward to grip and fasten to the post 108 at the desired point on the post 108. Once the collet 120 is secured onto the post 108, the receiver 112 is also fixed into place and ready for placement of the fixation rod 102 into the U-shaped channel of the receiver 112, followed by the addition of the nut 126 to secure the fixation rod 102 into place, completing the installation of the fixation hardware for a particular vertebra.

Further referring to FIG. 7, prior to adding the coupling mechanism and fixation rod, the pedicle screw 100 is first installed into the vertebra by screwing the pedicle screw 100 into place, with the use of the self-drilling configuration of pedicle screw 100 or other installation methods known in the art. Recess 110 may be used as the engagement point for the pedicle screw 100 for drilling the pedicle screw into the chosen vertebra. The pedicle screw 100 may be cannulated as shown by the passage 130 extending the length of the pedicle screw 100 with an opening at both the proximal end and the distal end of the pedicle screw 100.

Figure 8:
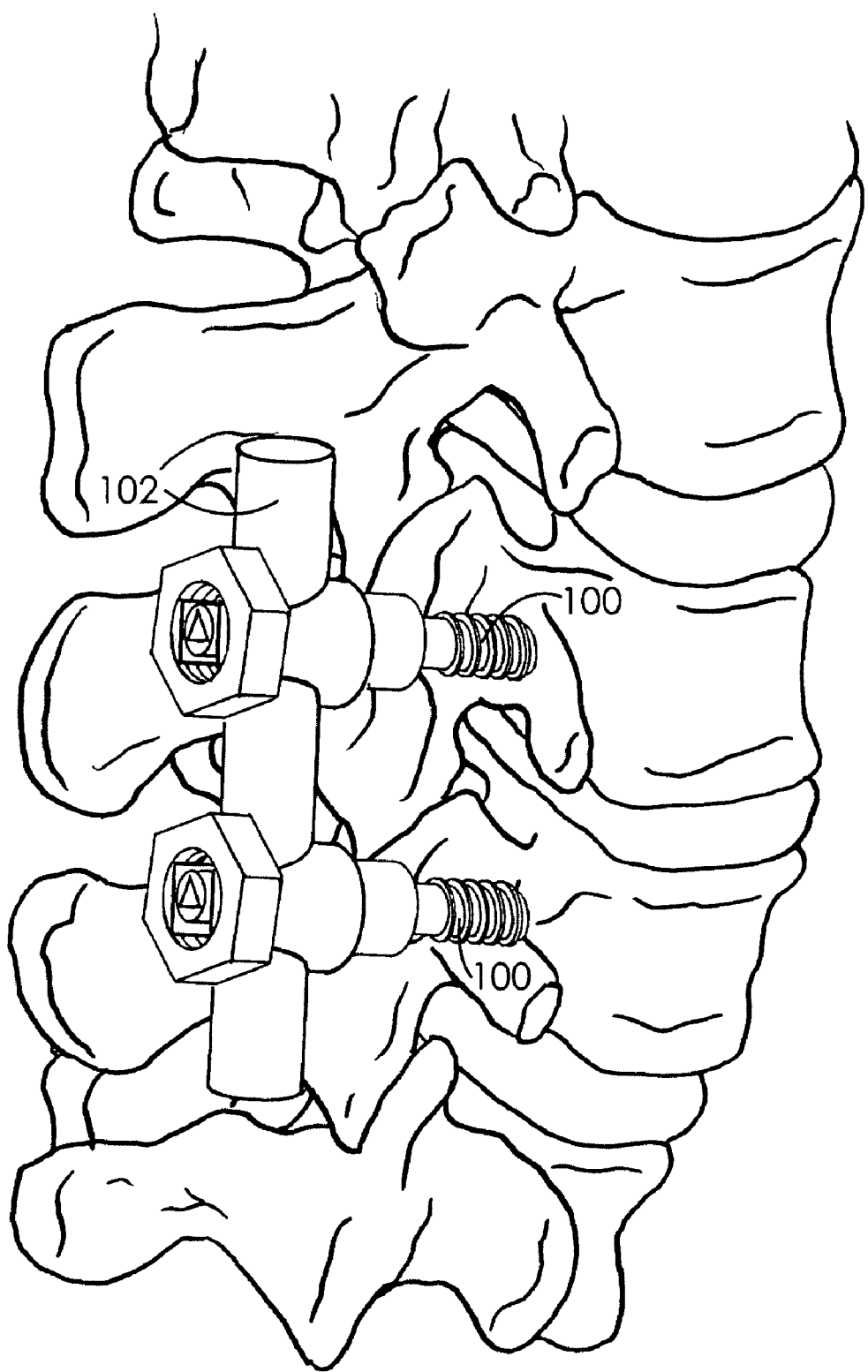
FIG. 8 is a perspective view of the spinal fixation system of FIG. 5 connected to a spine.

Referring to FIG. 8, the spinal fixation system depicted in FIGS. 5-7 is shown installed into a patient's spine. Note that different pedicle screws 100 may protrude from the spine at different heights depending on anatomical variations that may affect how deep the pedicle screw 100 is drilled into particular vertebra. Accordingly, the use of the collet 120 that may engage the pedicle screw 100 at various heights is useful to permit the fixation rod 102 to be utilized in connecting the various pedicle screws 100 together.

Referring to FIGS. 9-12, a spinal fixation system according to another embodiment of the invention is shown and includes a bone coupling element, shown as pedicle screw 200, a linking device, shown as fixation plate 202, and a coupling mechanism, the components generally shown as coupling mechanism 204.

Figure 10:
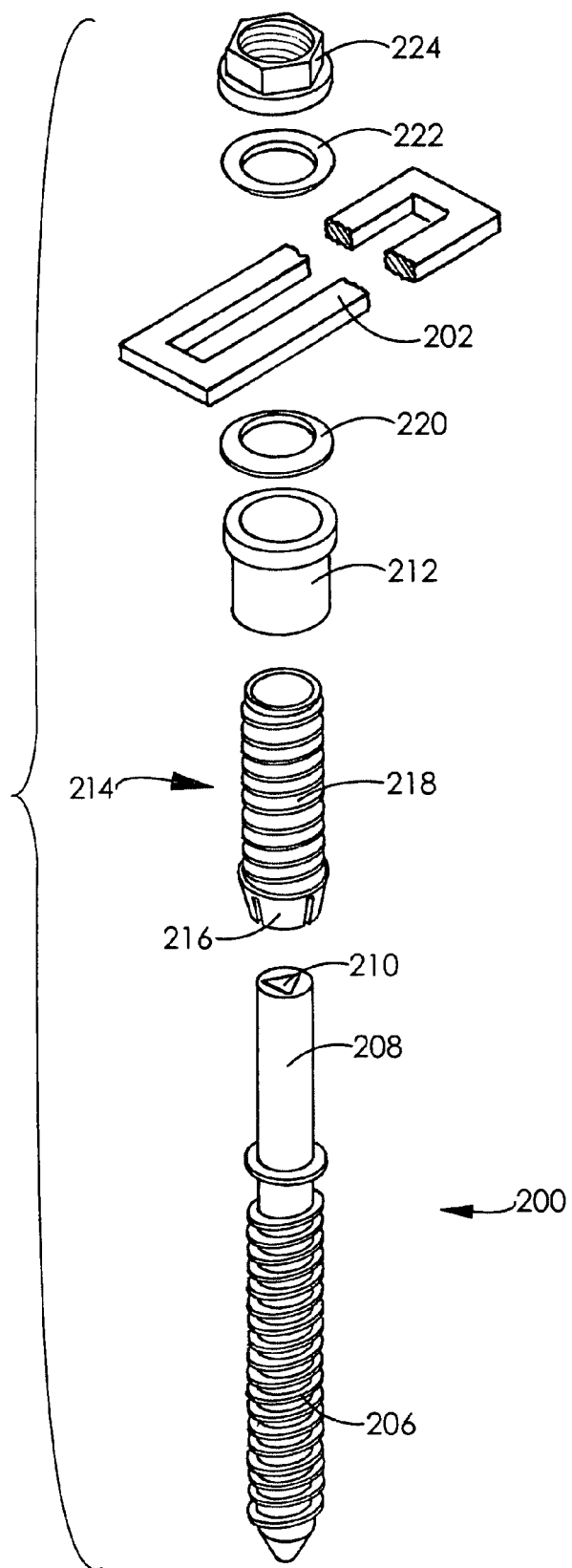
FIG. 10 is an exploded perspective view of the spinal fixation system of FIG. 9.

Referring to FIG. 10, the pedicle screw 200 is similar to the pedicle screws described with respect to other embodiments of the invention, and includes a threaded portion 206 and a non-threaded portion, shown as post 208. A recess 210 provides an interface for a tool or drill used to drill the pedicle screw 200 through a pedicle and into a vertebral body. A collet 214 has an elongated design with an inner aperture designed to be fitted over post 208, a set of compressible arms 216 designed to engage the pedicle screw 200, and a threaded portion 218. A collar 212 is designed to interface with the compressible arms 216. A pair of retaining rings 220, 222 provide an engagement point for the coupling mechanism with the fixation plate 202. A fastening device, shown as nut 224, has threads configured to engage with the threaded portion 218 of the collet 214.

Figure 11:
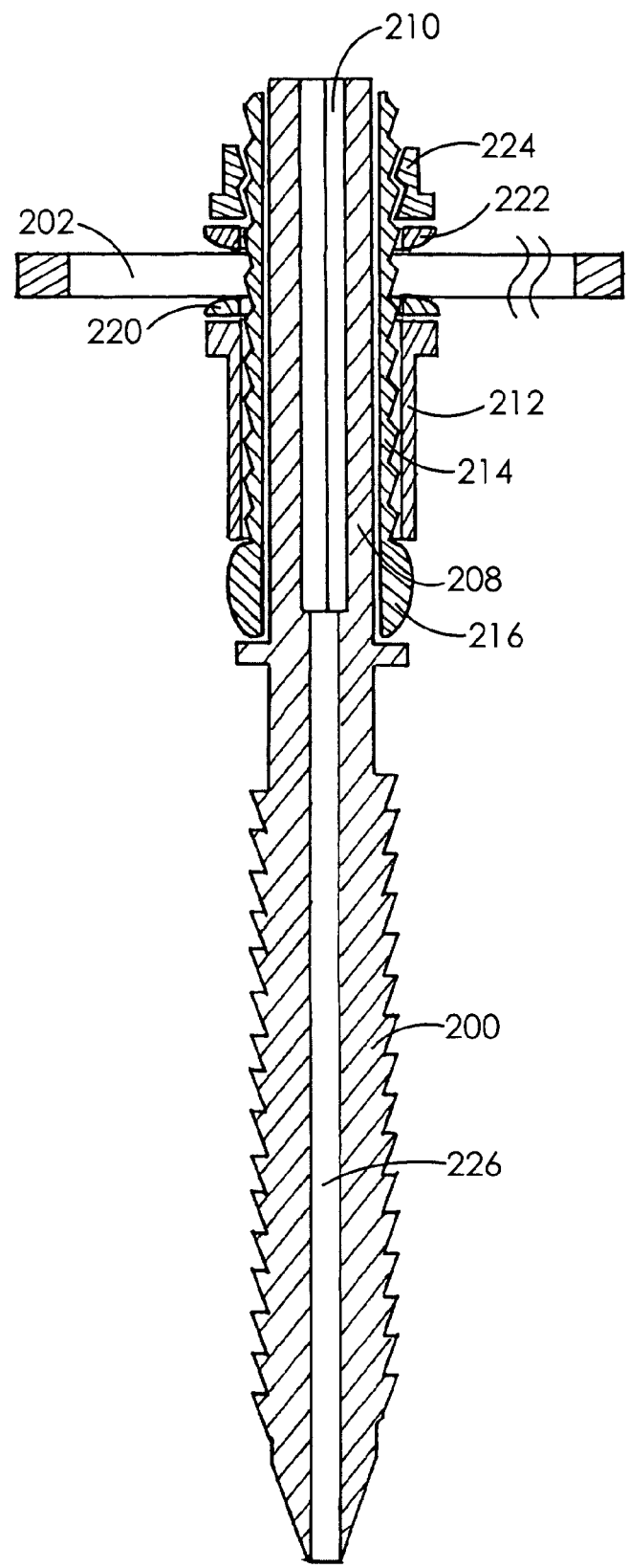
FIG. 11 is a sectional view of the spinal fixation system of FIG. 9 taken generally along line 11-11 of FIG. 9.

Referring to FIG. 11, in order to utilize the coupling mechanism to install the friction plate 202 to the pedicle screw 200, the collet 214, collar 212, and retaining ring 220 are placed over the post 208 after installation of the pedicle screw 200 into the chosen vertebra. The post 208 upon which the various components of the coupling mechanism are placed provides a guide and retaining function during assembly of the coupling mechanism to ease the attachment of the fixation plate 202.

After placement of the fixation plate 202 over the post 208, the retaining ring 222 and nut 224 are placed into position over the fixation plate 202. Tightening of the nut 224 performs two functions. First, the nut 224 engages the threads of the collet 214 and pulls the compressible arms 216 up into the collar 212 in order to depress the compressible arms 216 into the post 208, thereby locking the collet 214 onto the pedicle screw 200. Further, the nut 224 locks the fixation plate 202 relative to the pedicle screw 200 by compressing the fixation plate 202 between the retaining rings 220, 222. A passage, shown as passage 226 extends the length of the pedicle screw 200 generally extending from the recess 210.

The embodiment of the invention shown in FIGS. 9-12 requires only one component to be screwed into place, the nut 224, which connects both the fixation plate 202 and the collet 214 to the pedicle screw 200. The rest of the components of the coupling mechanism 204 slide into place over the post 208. Reducing the number of components that must be screwed together in the assembly of the spinal fixation system is advantageous as cross-threading of components that are screwed together is a problem encountered in surgery and reducing the number of components that must be screwed together addresses that issue. Further, only requiring one pair of components to be screwed together per pedicle screw may reduce the time necessary to assemble the spinal fixation system, thereby reducing the overall time required for the operation.

Figure 9:
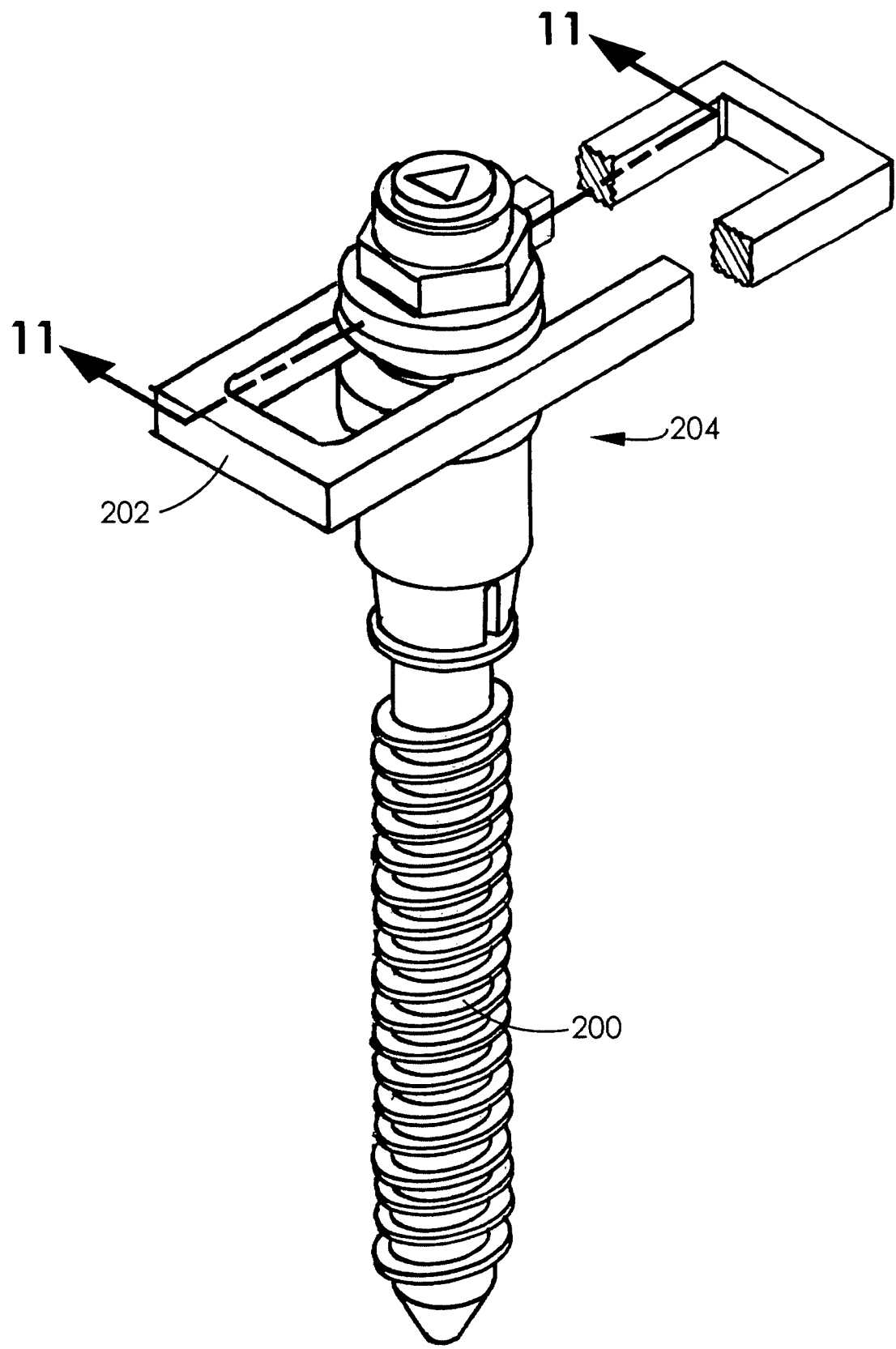
FIG. 9 is a perspective view of a spinal fixation system.
Figure 12:
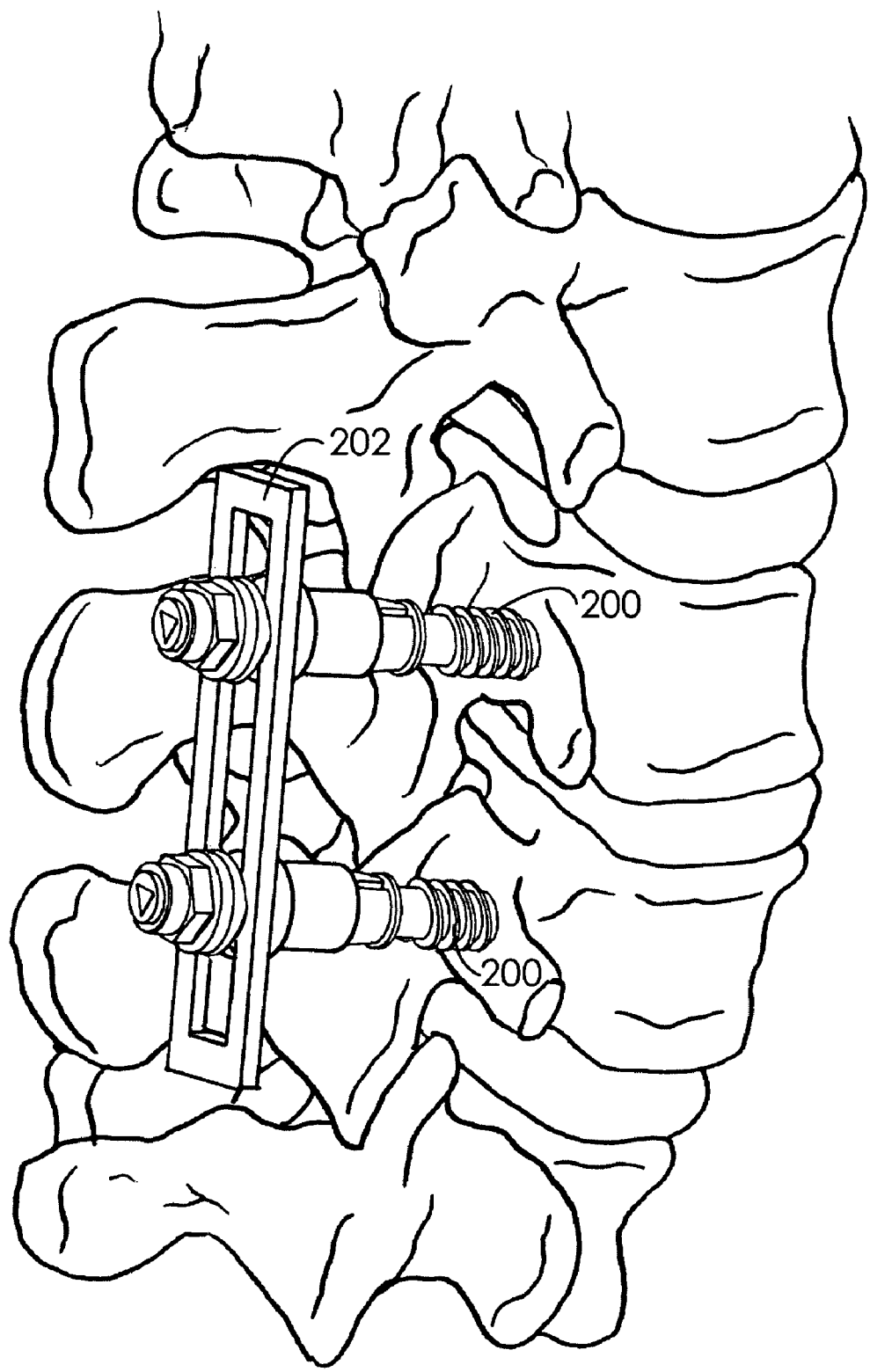
FIG. 12 is a perspective view of the spinal fixation system of FIG. 9 connected to a spine.

Referring to FIG. 12, the invention shown in FIGS. 9-11 is shown as installed into a spine, with two pedicle screws 200 shown for exemplary purposes although a greater number of pedicle screws 200 may be utilized, depending on the number of vertebrae to be fixed to one another. The fixation plate 202 may be of various lengths depending on the number of pedicle screws 200 used. Because the collet 214 may engage the pedicle screw 200 at various points, variations in the heights of the installed pedicle screws 200 may be addressed in order to result in a continuous height of the fixation plate 202 by simply varying the points of engagement of the coupling mechanism 204 on different pedicle screws 200.

Referring to FIGS. 13-16, a spinal fixation system according to another embodiment of the invention includes a bone-coupling element, shown as pedicle screw 300, a fixation element or linking device, shown as fixation rod 302, and a coupling mechanism, generally shown as coupling mechanism 304.

Figure 14:
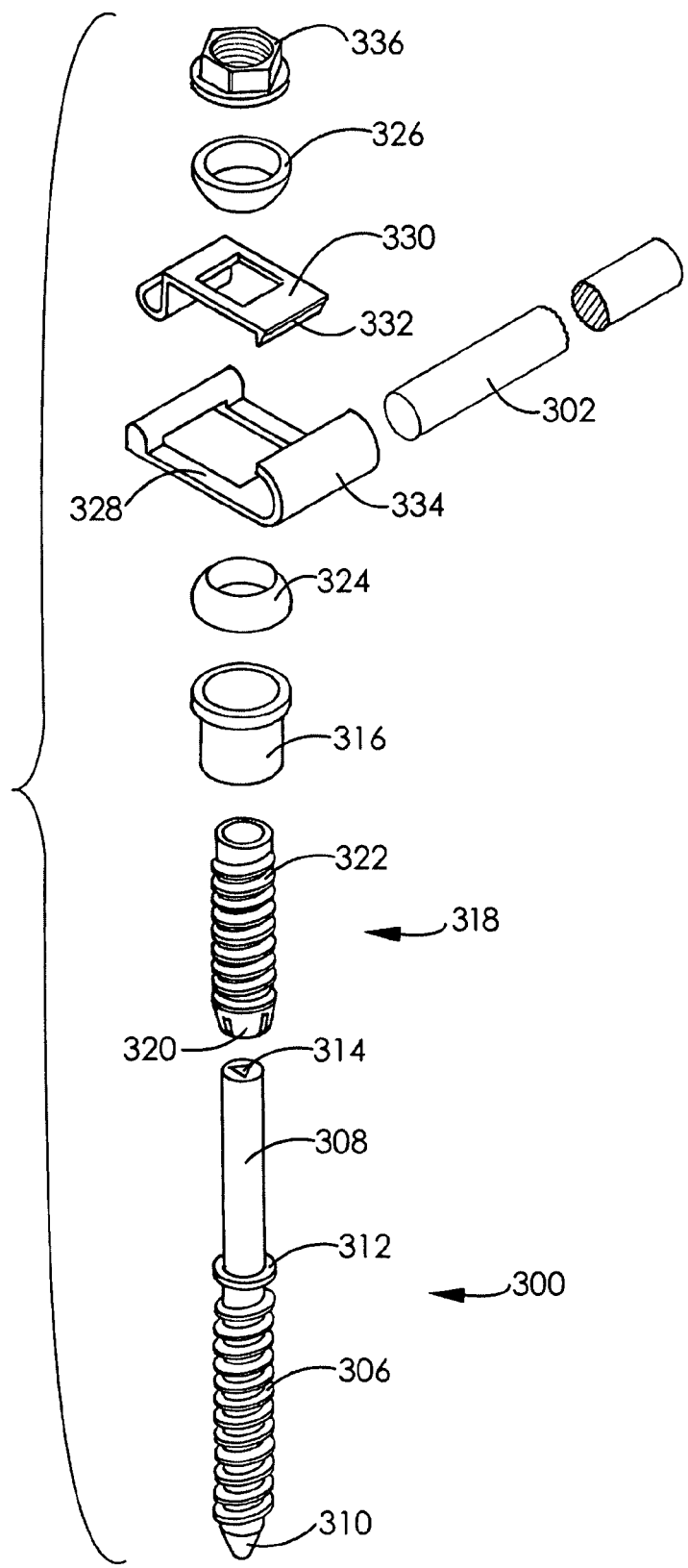
FIG. 14 is an exploded perspective view of the spinal fixation system of FIG. 13.

Referring to FIG. 14, the pedicle screw 100 includes a threaded portion 306 and a non-threaded portion shown as post 308. The threaded portion 306 is bounded by a distal tip 310 and a flange 312. A recess 314 extends into the post 308 for engagement by a tool or drill. A collet 318 has an interior channel sized to fit over the post 308. The collet 318 includes a threaded portion 322 and a number of compressible arms 320. A collar 316 is sized to fit over the collet 318. A receiver for the fixation rod 302 includes a pair of plates, shown as lower portion 328 and upper portion 330. The plates are hinged so that the upper portion 330 is pivotally attached to the lower portion 328. The lower portion 328 includes a hook 334 for engagement with the fixation rod 302 and the upper portion 330 includes an engagement arm 332 that is used to lock the fixation rod 302 into place. A pair of retaining rings 324, 326 are disposed on either side of the receiver and a fastening device, shown as nut 336, is configured to secure the entire coupling mechanism together by threading onto collet 318.

Figure 15:
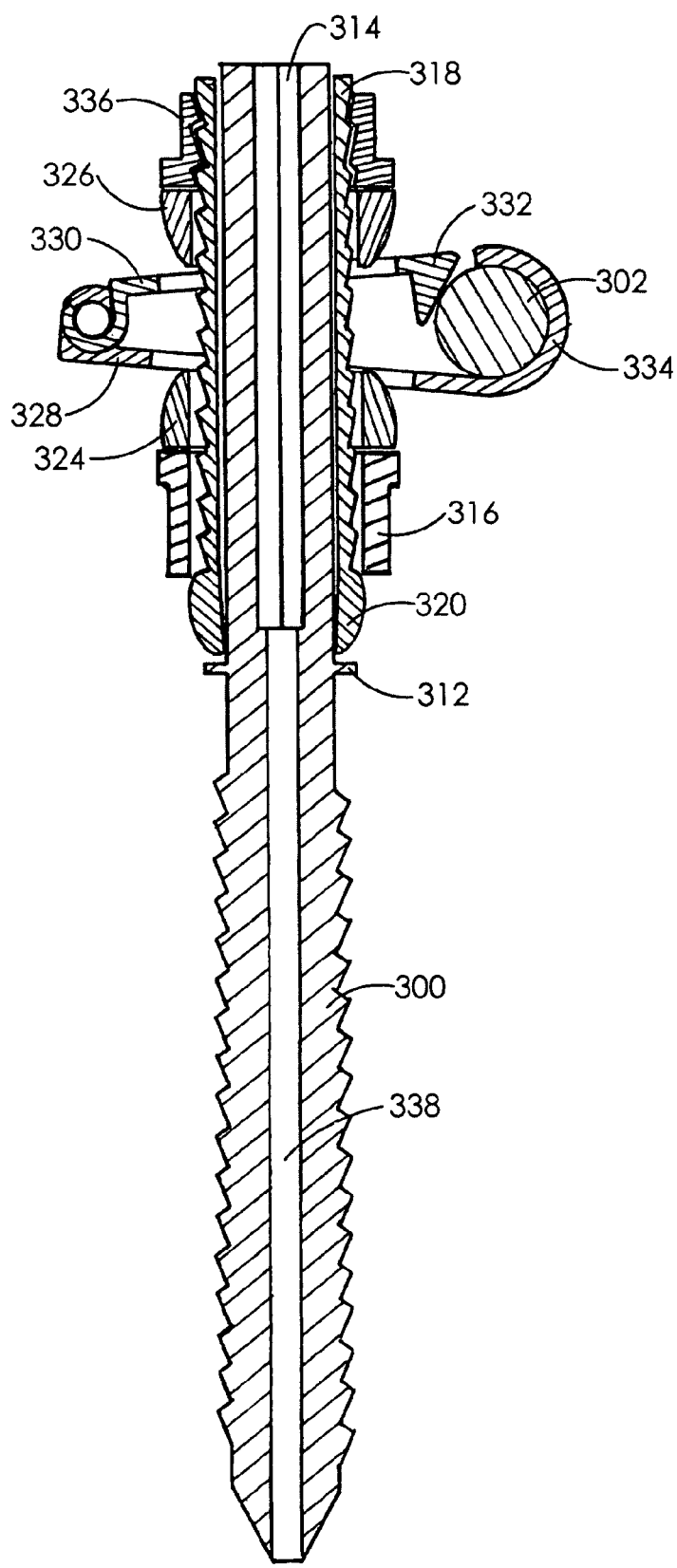
FIG. 15 is a sectional view of the spinal fixation system of FIG. 13 taken generally along line 15-15 of FIG. 13.

Referring to FIG. 15, the coupling mechanism is secured to the pedicle screw 300 in a similar fashion to that described with respect to the embodiment depicted in FIGS. 9-12 via the tightening of nut 336 onto collet 318, thereby pulling the compressible arms 320 up into the collar 316, thereby fixing the collet 318 into place at the selected height upon pedicle screw 300. Engagement with the fixation rod 302 however is handled differently by using the components of the receiver to attach the coupling mechanism to the fixation rod 302 with the fixation rod 302 offset from the longitudinal axis of the pedicle screw 300. Further referring to FIG. 15, tightening the nut 336 onto the collet 318 not only secures the collet 318 into place on the pedicle screw 300 but also drives the upper portion 330 downward toward the lower portion 328 until the engagement arm 332 engages the fixation rod 302 to fix the fixation rod 302 into place relative to the coupling mechanism and the pedicle screw 300. Accordingly, the fastening device or nut 336 performs two coupling functions that require at least two fastening components in other designs. During assembly, the various components of the coupling mechanism are stacked onto the pedicle screw 300 using the post 308 as a guide after installing the pedicle screw 300 into the bone. The components of the receiver are configured to be installed on the post 308 along a range of positions offset from the longitudinal axis of the pedicle screw 300 to allow for some variability in the angle of the pedicle screw 300 after installation into the chosen vertebra. Further, like the earlier described embodiments, the coupling mechanism may be adjusted along the longitudinal axis of the pedicle screw 300 to account for variability in the height of the installed pedicle screw 300.

Figure 13:
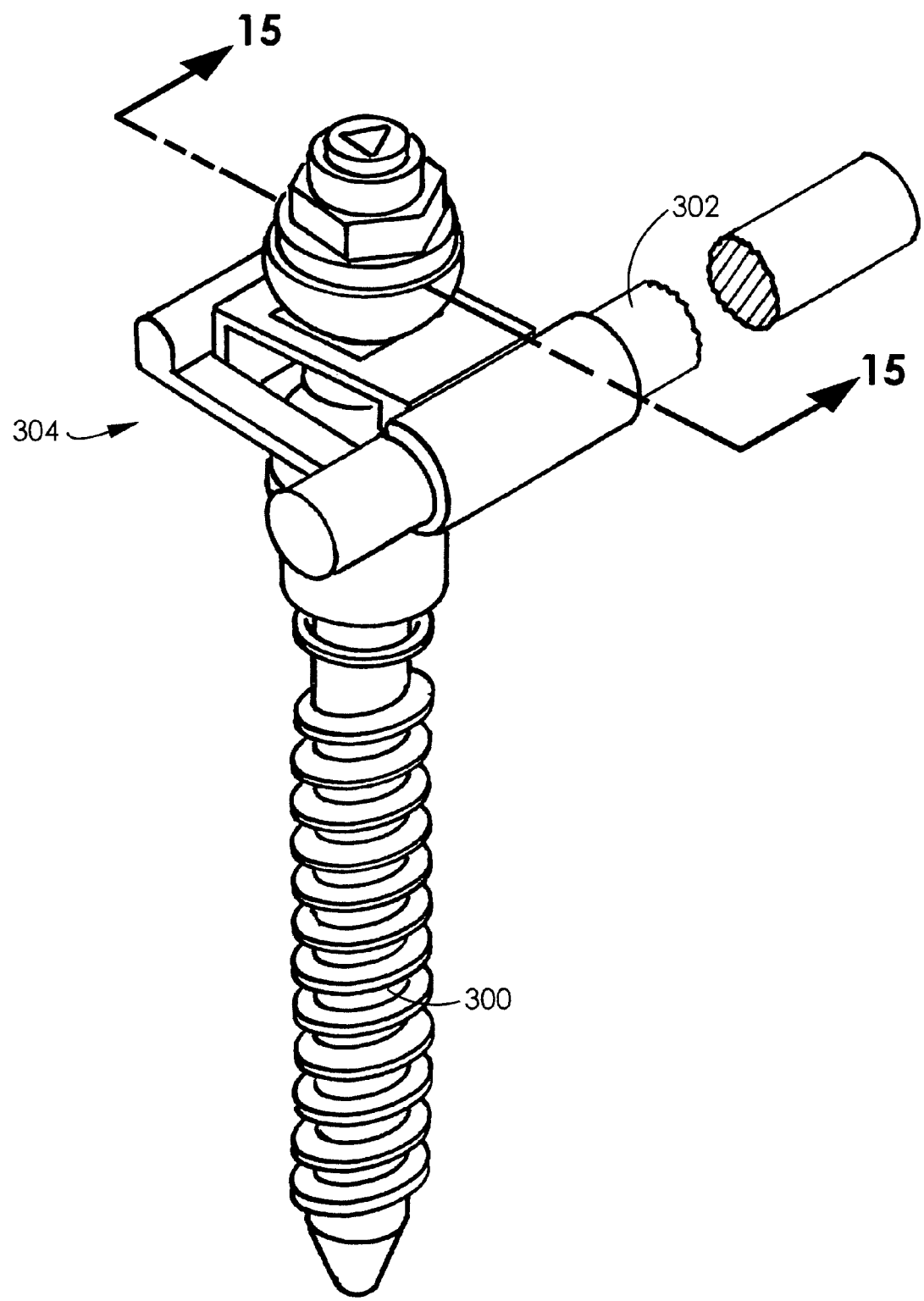
FIG. 13 is a perspective view of a spinal fixation system.
Figure 16:
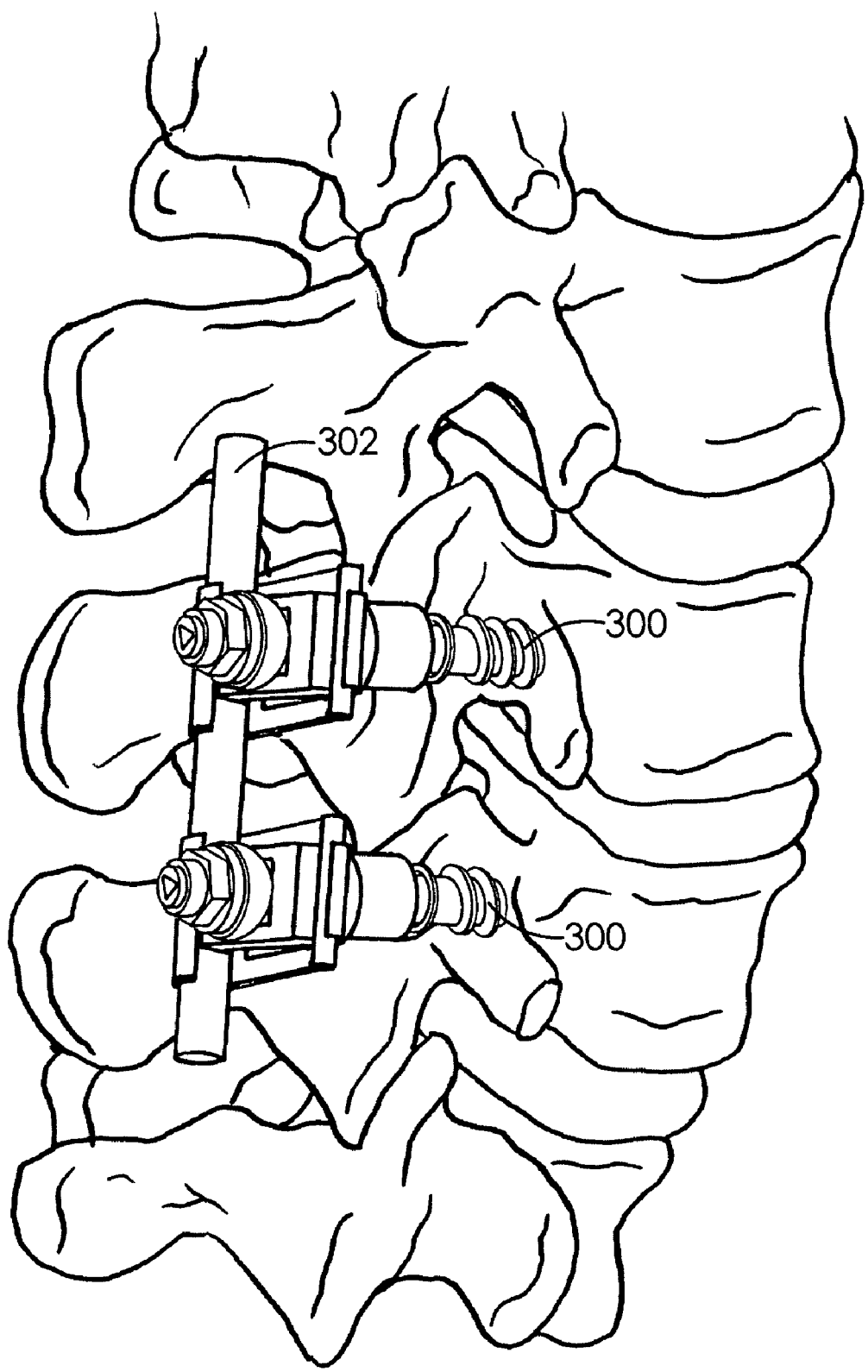
FIG. 16 is a perspective view of the spinal fixation system of FIG. 13 connected to a spine.

Referring to FIG. 16, the spinal fixation system shown in FIGS. 13-15 may be installed in the spine with the fixation rod 302 oriented on either side of the pedicle screws 300 by changing the position of the receiver lower portion 328 and upper portion 330. Although two pedicle screws 300 are shown as fixed by fixation rod 302, additional pedicle screws 300 may be installed in a line with a fixation rod 302 having the appropriate length to connect the pedicle screws 300.

Referring to FIGS. 17-22, in an exemplary embodiment of the invention, a pedicle screw 400 may be used in conjunction with a driver, shown as drill 414, and holding device 430. As in earlier described embodiments, the pedicle screw 400 includes a threaded portion 402, a non-threaded post 404, a tip 406, a flange or ridge 410, and a recess 412. The drill 414 includes a shaft 416 sized to fit within a passage 408 (see FIG. 19), a portion having cutting edges 418, and a drill tip 420. Referring to FIGS. 3, 7, 11, and 15, the pedicle screws shown in various embodiments of the invention are cannulated to include passages 54, 130, 226, and 338 to accommodate drills such as drill 414. Accordingly, the drill 414 may function as a drill and as a driver for turning the screw. The term "driver" is intended to generically refer to a drill or turning tool or a tool having both functions. A keyed segment 422 of the drill is shaped to lock into recess 412 so that when the drill 414 is rotated, the pedicle screw 400 is also rotated. An expanded segment 424 is sized to rest upon the top of post 404, and has an outer diameter that is the same as that of post 404 in a preferred embodiment. An upper keyed segment 426 provides an interface for a drill or other turning tool used to turn the drill 414 and the pedicle screw 400.

Figure 17:
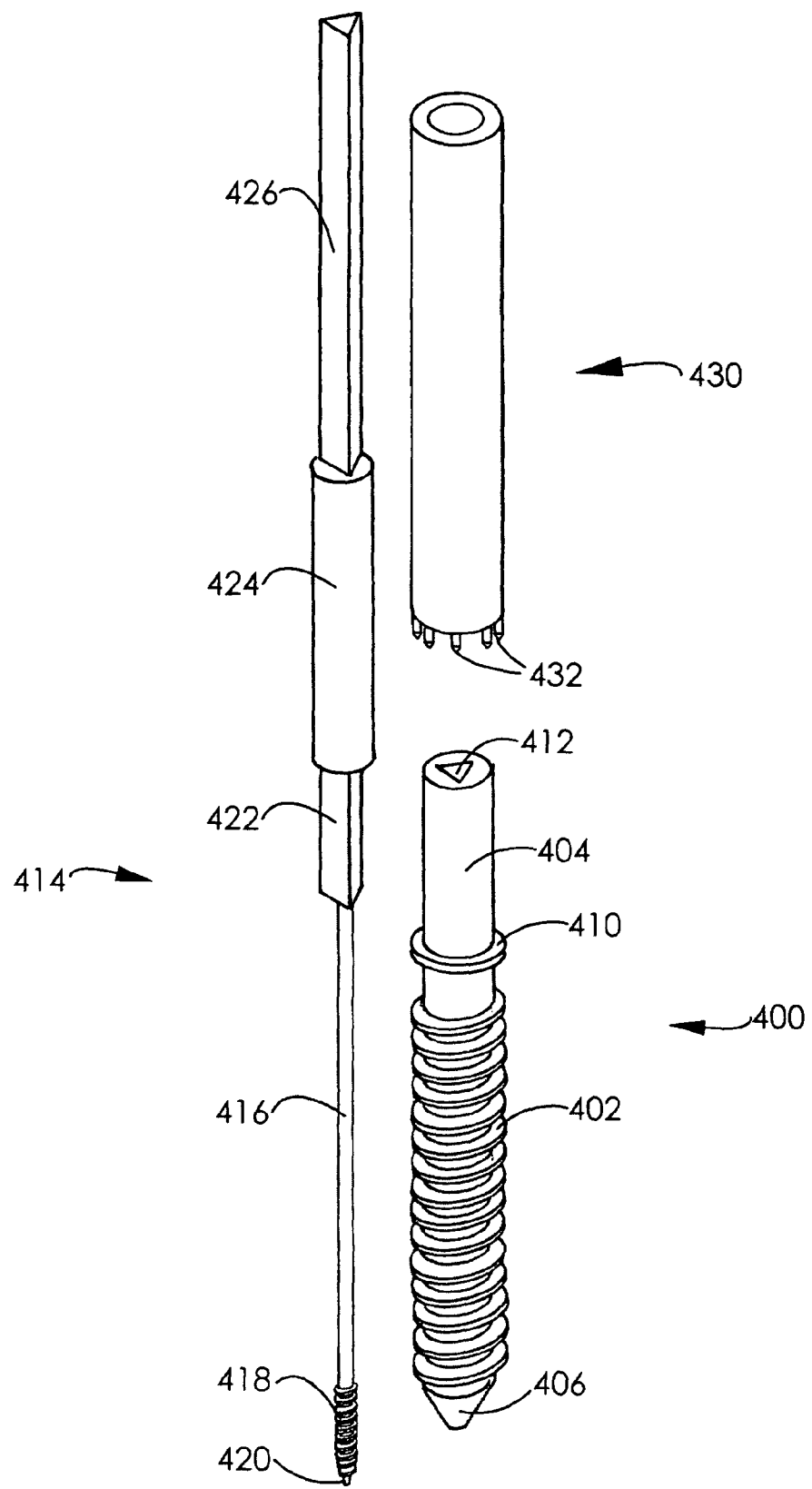
FIG. 17 is a perspective view of a pedicle screw and drill assembly.
Figure 19:
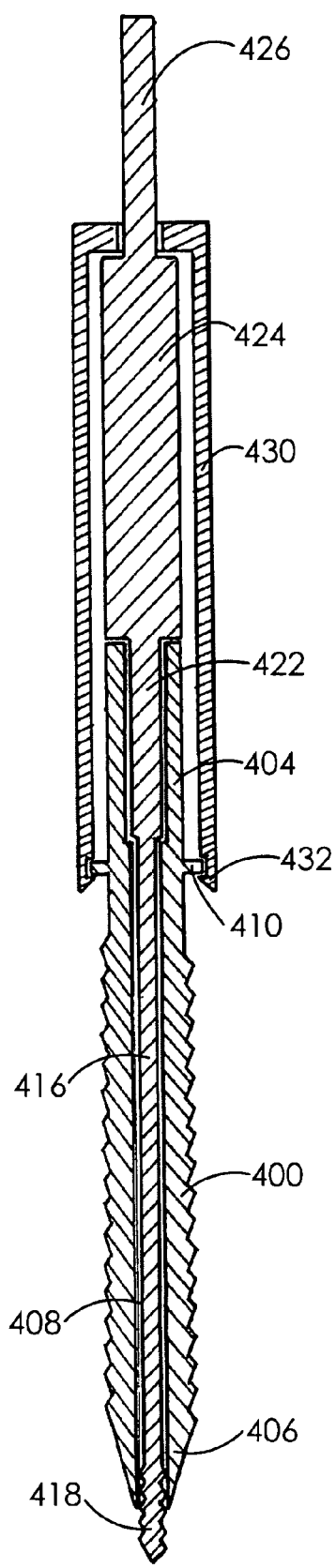
FIG. 19 is a sectional view of the pedicle screw and drill assembly of FIG. 18.

Further referring to FIG. 17, a holding device 430 is shown as having a cylindrical shape and an attachment mechanism, shown as a number of prongs 432, extending from the bottom of the holding device 430 and intended to snap over the ridge 410 to connect the holding device 430 to the pedicle screw 400. Referring to FIG. 19, the top of the holding device 430 may be shaped to engage expanded segment 424 to lock the drill 414 into place in the pedicle screw 400.

Figure 18:
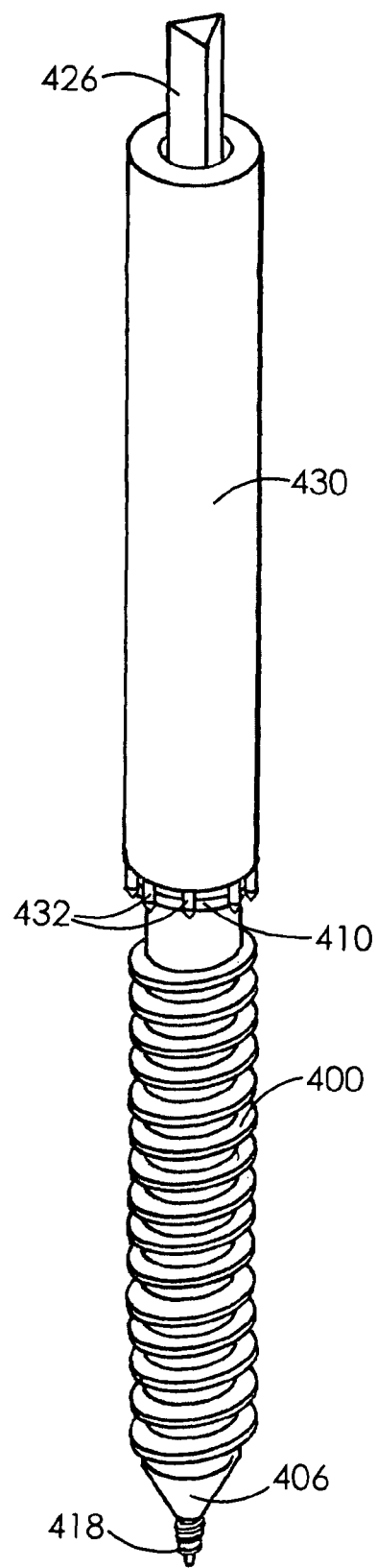
FIG. 18 is a perspective view of the pedicle screw and drill assembly of FIG. 17 as assembled for use.

Referring to FIG. 18, once assembled together, the pedicle screw 400, drill 414, and holding device 430 create an efficient tool for drilling the pedicle screw into a selected vertebra. The drill tip 420 extends from the distal opening of the passage in the pedicle screw at the pedicle screw tip 406 to aid in the insertion of the pedicle screw 400. The smaller diameter cutting edges 418 and sharp cutting tip 420 may be desired by a surgeon when inserting the pedicle screw 400 to provide a more accurate placement and initial drilling point for the pedicle screw 400, eliminating the necessity of first drilling a pilot hole and utilizing a guide wire to guide the pedicle screw. Inserting a separate guide wire with a separate drill bit requires additional steps in the surgery and additional components, complicating and perhaps lengthening the overall surgery. The holding device 430 aids in the manipulation of the pedicle screw 400 and drill 414 by preventing the drill 414 from disengaging from the pedicle screw 400 during the insertion process.

Referring to FIG. 19, the drill 414 and holding device 430 may be assembled together with the pedicle screw 400 prior to connecting the pedicle screw 400 to the spine and may be assembled by sliding the components together and snapping the holding device 430 onto the pedicle screw 400 without having to screw various components together.

Figure 20:
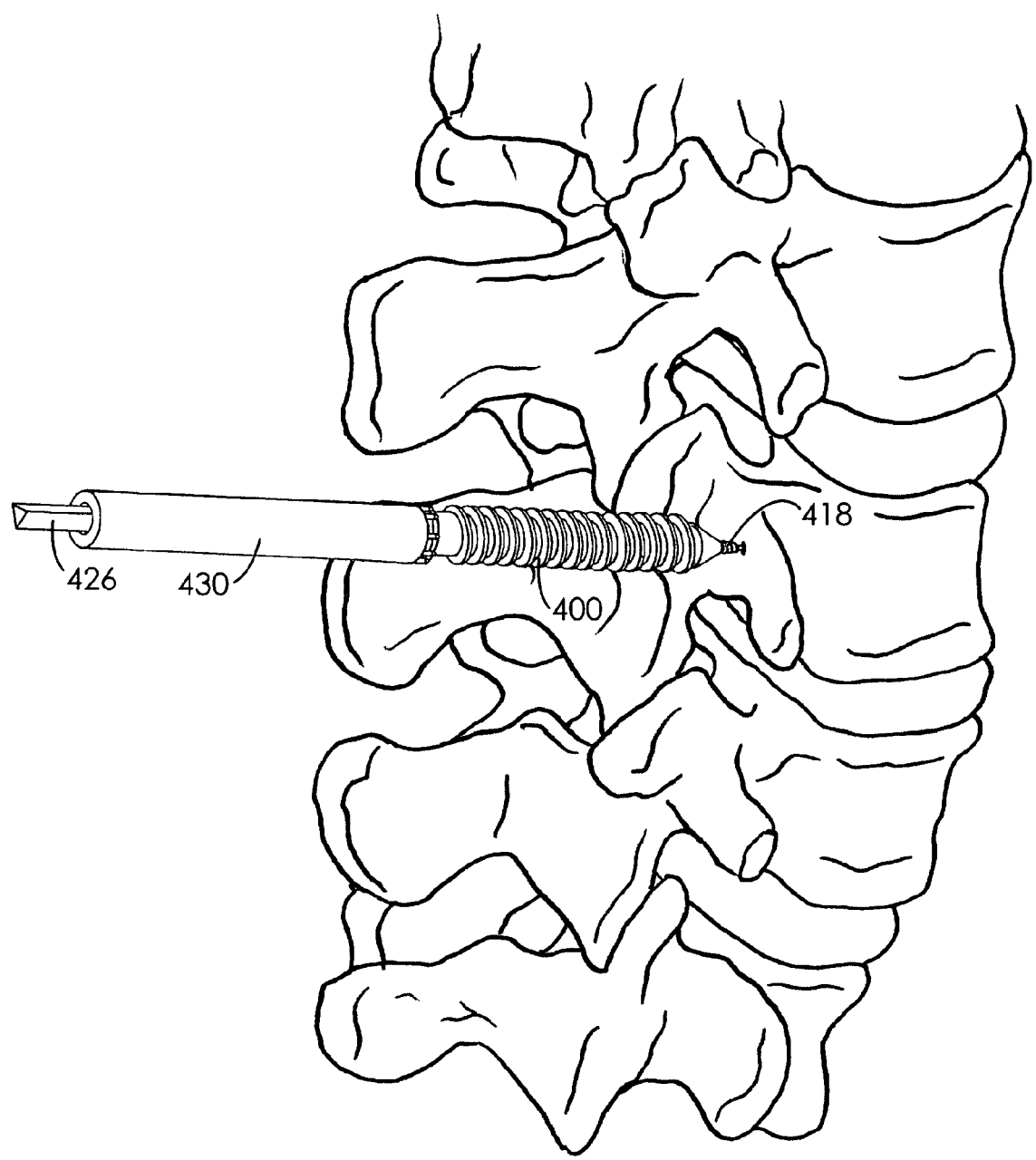
FIG. 20 is a perspective view of the pedicle screw and drill assembly of FIG. 18 positioned for use on a spine.

Referring to FIG. 20, the assembled device depicted in FIG. 18 may be utilized to drill the pedicle screw 400 into a chosen location in the spine utilizing the drill 414 in combination with the pedicle screw 400. The drill tip 420 aids in selecting a precise location for drilling the hole for the pedicle screw 400.

Figure 21:
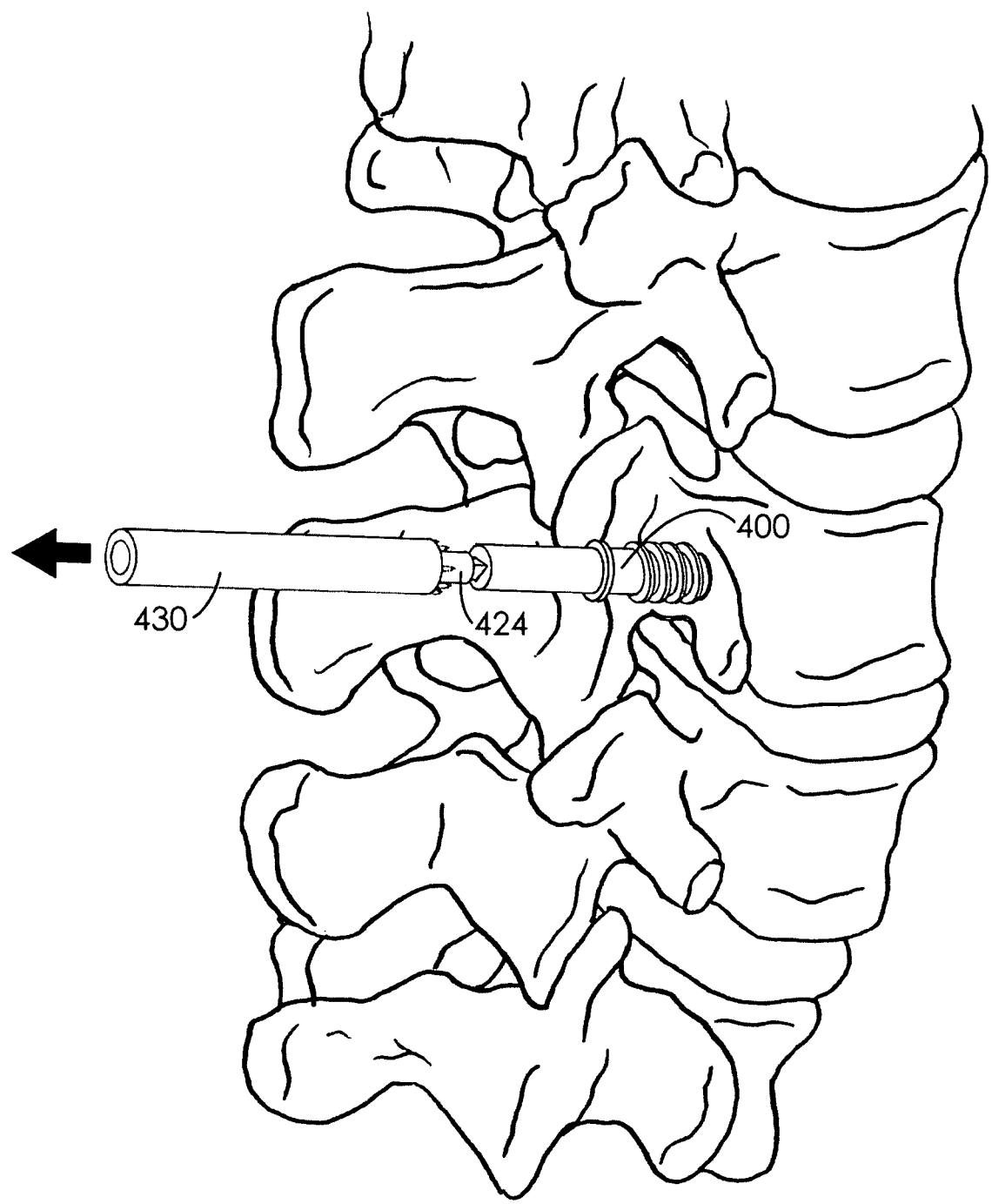
FIG. 21 is a perspective view of the pedicle screw and drill assembly of FIG. 20 after connection of the pedicle screw to the spine.
Figure 22:
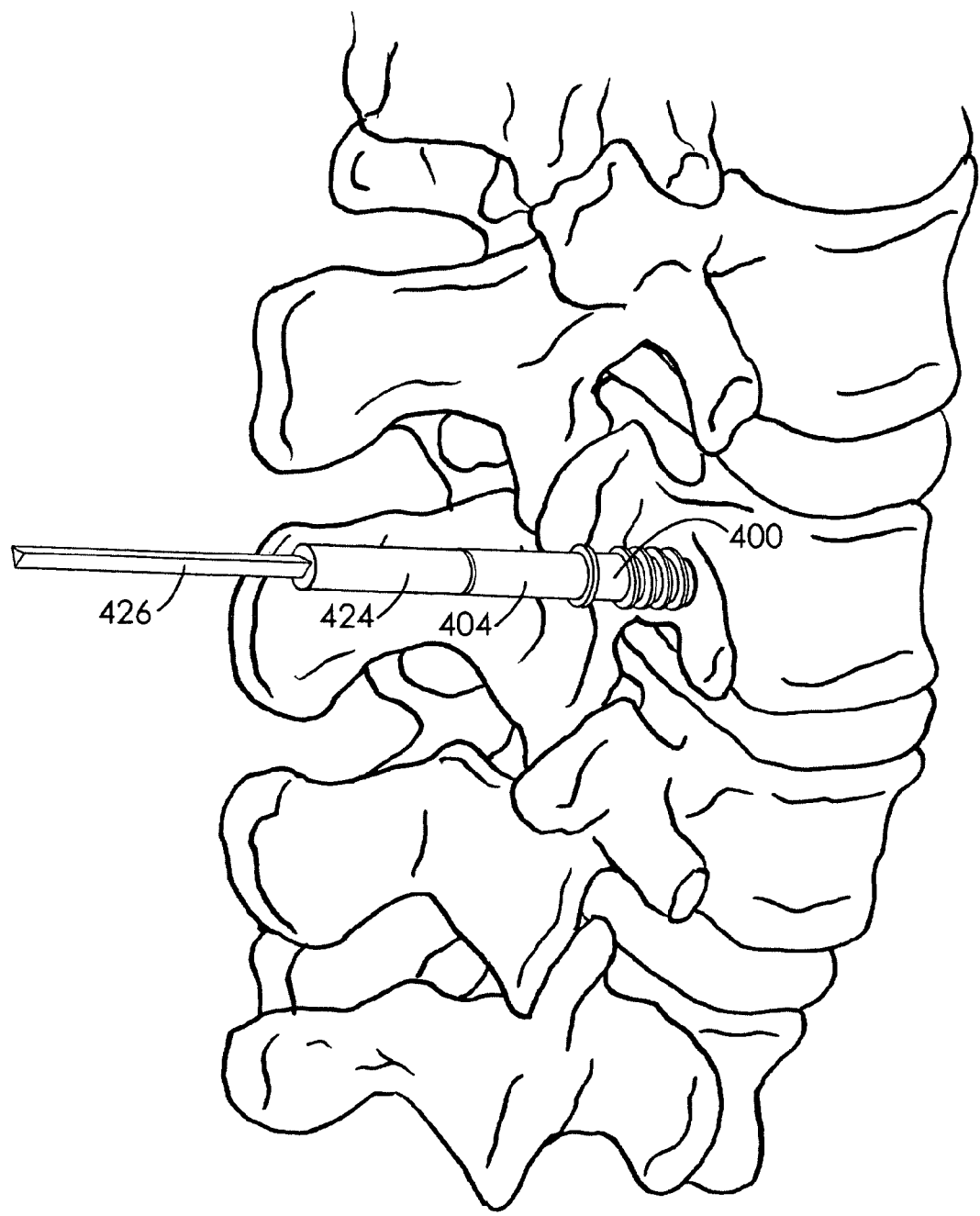
FIG. 22 is a perspective view of a pedicle screw and associated drill assembly connected to a spine.

Referring to FIG. 21, once the pedicle screw 400 has been screwed into the vertebra, the holding device 430 may be removed from the pedicle screw 400 by disengaging the prongs 432, which in a preferred embodiment may be disengaged by pulling the holding device 430 away from the pedicle screw 400. Referring to FIG. 22, once the holding device 430 has been removed from the pedicle screw 400, the drill 414 remains. In a preferred embodiment, the drill may be removed from the pedicle screw 400 by pulling the keyed segment 422 out of the recess 412. However, the user may elect to leave the drill 414 in place (or replace the drill 414 with another driver configured to be inserted into the passage 408) during assembly of the coupling mechanism as described below.

Figure 23:
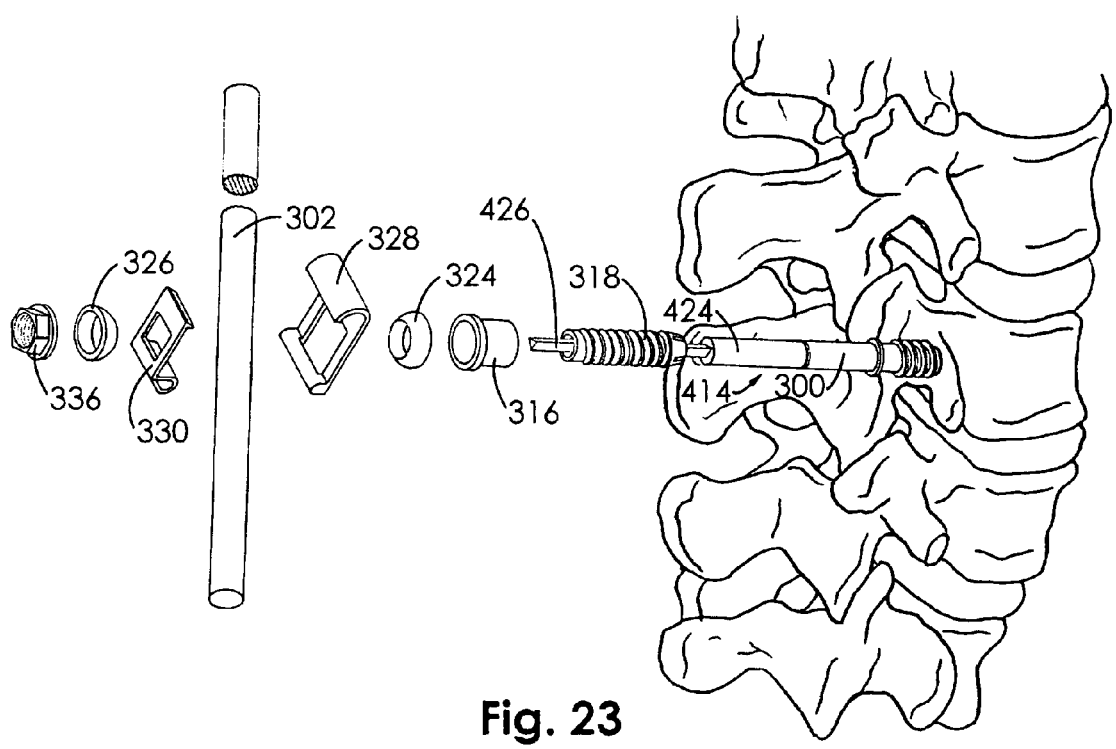
FIG. 23 is an exploded perspective view of the components of a spinal fixation system.

Referring to FIG. 23, the drill 414 may be utilized in conjunction with a pedicle screw after installation of the pedicle screw to aid in the installation of various coupling components. In the embodiment depicted in FIG. 23, the components of the coupling mechanism 304 shown in FIGS. 13-16 are shown for exemplary purposes only. A similar approach may be utilized with the other coupling mechanisms and components shown with respect to the spinal fixation systems described in other embodiments of the invention. The drill 414, including upper keyed segment 426 and expanded segment 424, is sized to provide a guide for the coupling components utilized to attach the pedicle screw 300 to the fixation rod 302. Accordingly, after installation of the pedicle screw 300, a surgeon may elect to leave the drill 414 in place and utilize the drill 414 to serve as a guide for installation of the collet 318, collar 316, retaining ring 324, receiver lower portion 328, and upper portion 330, retaining ring 326, and nut 336. Alternatively, the surgeon may remove the drill 414 and insert a similarly configured driver into the screw to function as the guide.

In a minimally invasive surgical approach, use of the drill 414 as a guide for the coupling components may be especially useful because a small percutaneous aperture may be made for each installed pedicle screw, and the drill 414 may extend out of the patient's body to aid in placement of the coupling components. Without the aid of the drill 414 as a guide in minimally invasive surgical approaches, placement of the components directly onto the post 308 may be difficult due to the small size of the percutaneous aperture and obstructed visual access.

Figure 24:
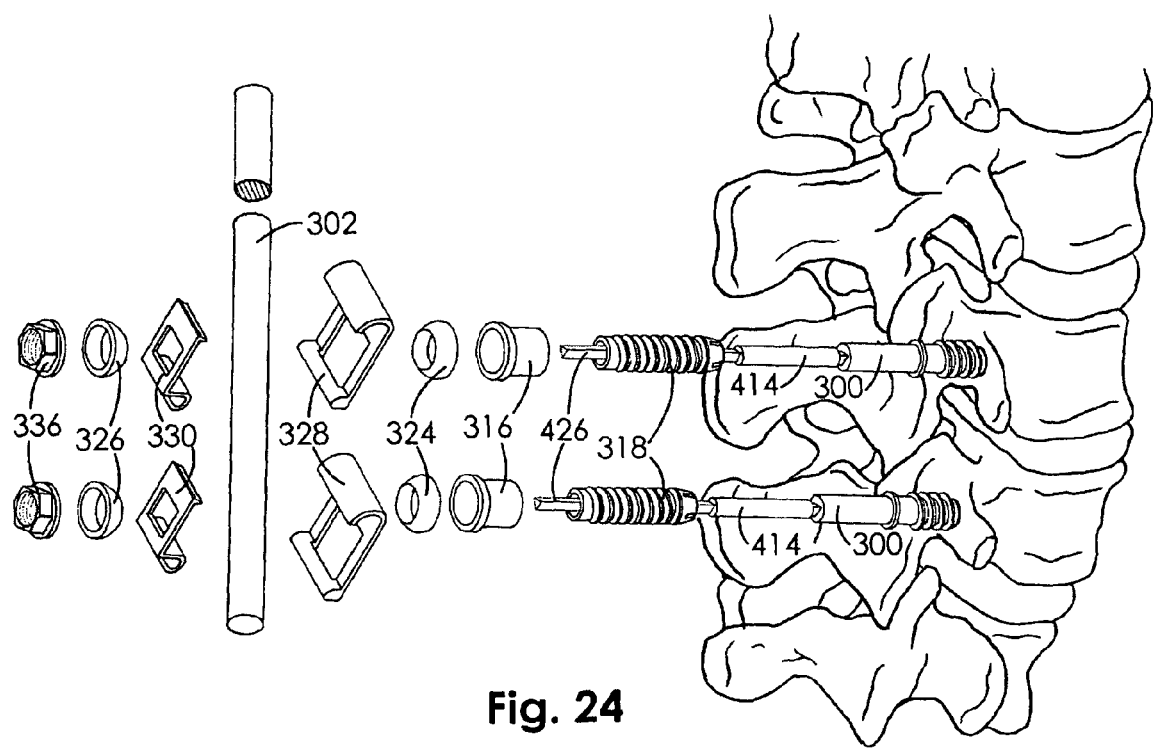
FIG. 24 is an exploded perspective view of a spinal fixation system.

Referring to FIG. 24, expanding on the concept presented in FIG. 23, the drill 414 may be left in place in multiple pedicle screws 300 after the installation of each pedicle screw 300. Such an approach requires the use of multiple drills 414 so that during a surgical operation, each pedicle screw 300 may be installed with a separate drill 414, the drill 414 left into place for installation of coupling components for each pedicle screw 300. FIG. 24 depicts two pedicle screws 300 requiring coupling components for exemplary purposes but the concept may be utilized with any number of pedicle screws.

Figure 25:
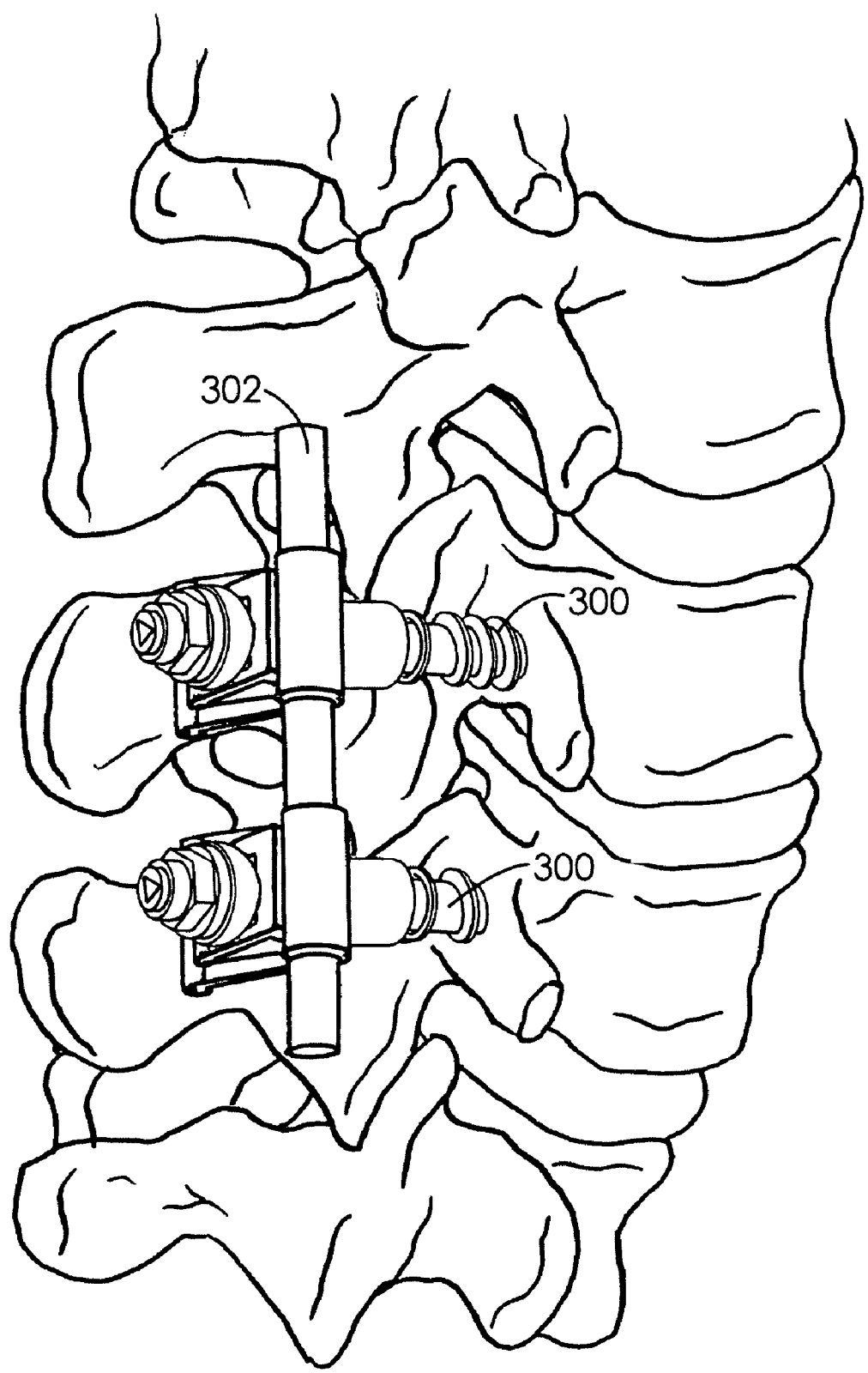
FIG. 25 is a perspective view of the spinal fixation system of FIG. 24 with the components assembled.

Referring to FIG. 25, after the coupling components have been put into place and attached to the fixation rod 302, the individual drills 414 may be removed by pulling the drills out of the pedicle screws, leaving the installed components (including the pedicle screws 300) in place. One reason for the utilization of a separate drill 414 which is removable from the installed fixation system is that the surgeon may not wish to utilize components of a fixation system that include a permanently installed sharp cutting tip.

Figure 26:
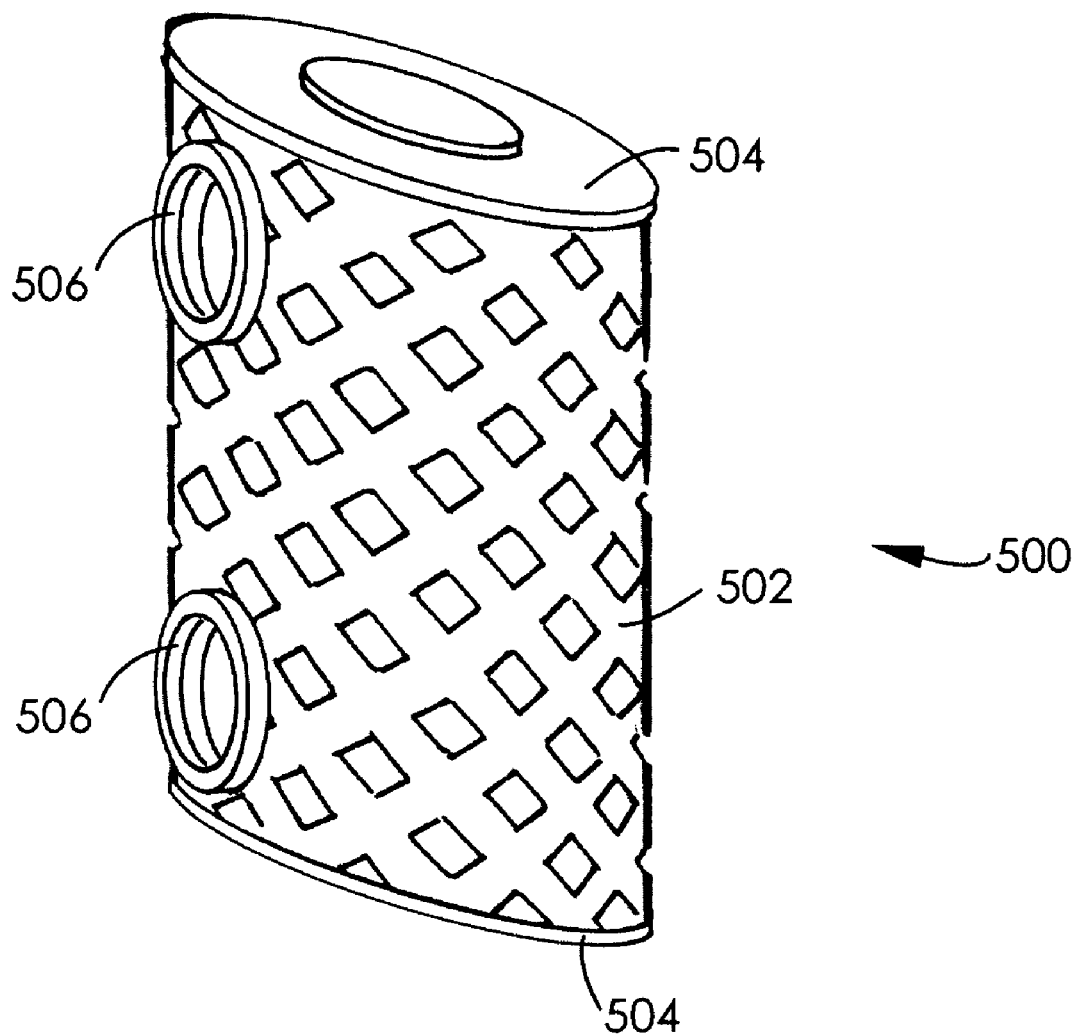
FIG. 26 is a perspective view of a bone graft implant.
Figure 27:
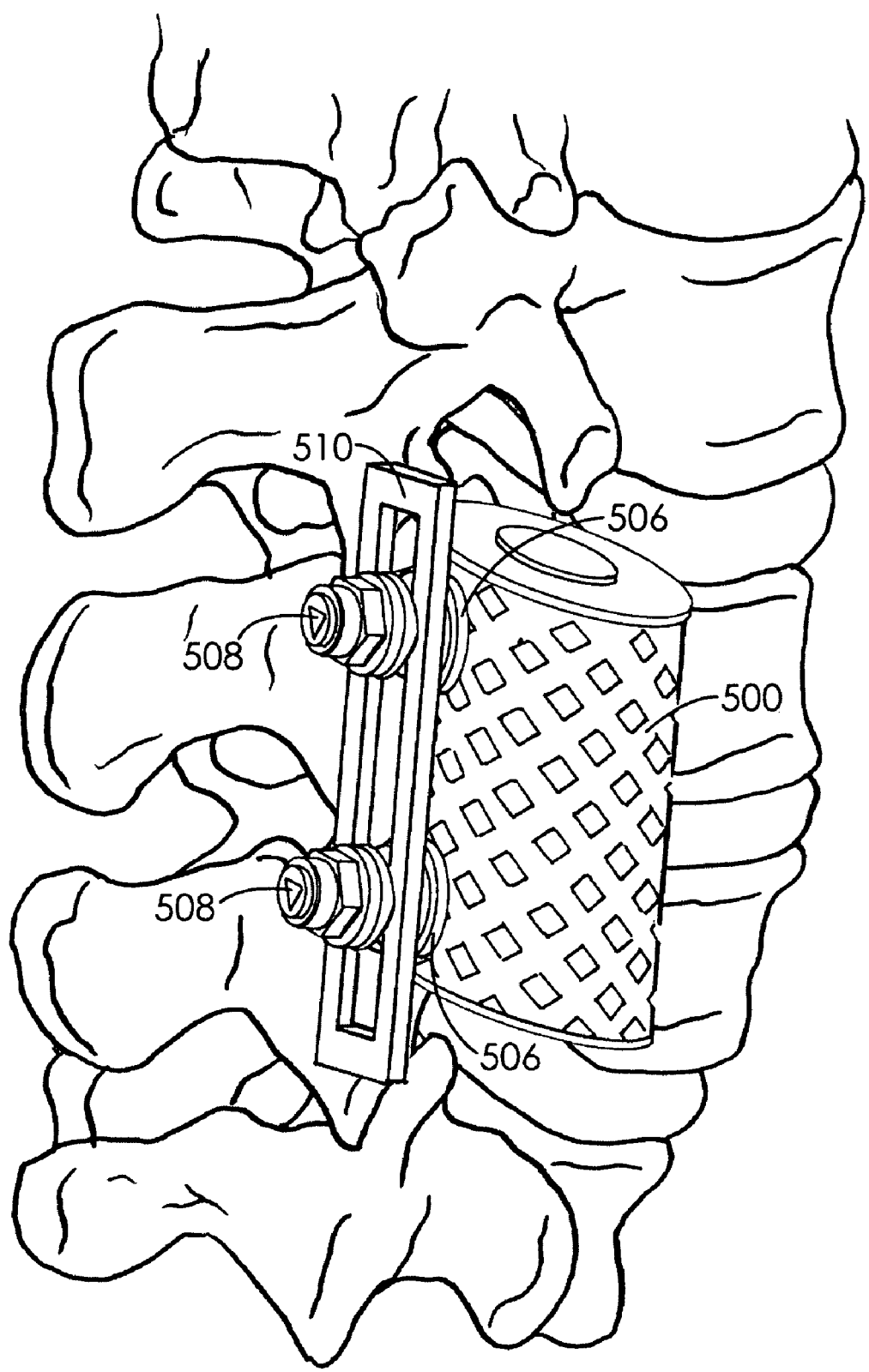
FIG. 27 is a perspective view of a bone graft implant in use as part of a spinal fixation system.

Referring to FIGS. 26 and 27, in accordance with one embodiment of the invention, the spinal fixation system includes a mechanism for inserting bone graft material as part of a spinal fusion procedure, shown as bone graft implant 500. The bone graft implant 500 includes a reservoir, shown as a nylon or fiber mesh bag 502, having a pair of end caps 504. A number of apertures, shown as grommets 506, may be placed in the bag 502 on both sides of the bag 502 to permit installation of the bag 502 over a number of pedicle screws. The bag 502 may be filled with a bone graft material and utilized to enhance spinal fusion.

Referring to FIG. 27, in one embodiment, the bone graft implant 500 may be placed over a number of pedicle screws 508 prior to installation of a linking device, shown as fixation plate 510, and the associated coupling mechanism. In the embodiment depicted in FIG. 27, the pedicle screws, fixation plate, and coupling mechanism are similar to the components shown in the spinal fixation system embodiment described above with respect to FIGS. 9-12. In a surgical procedure, the pedicle screws 508 may be installed into the selected vertebrae, followed by installation of the bone graft implant 500, which has already been filled with bone graft material, over the posts of the pedicle screws 508. The grommets 506 provide a mechanism for maintaining the placement of the bone graft implant 500 in the proper location and also provides an effective guide mechanism where visual access is impaired because the grommets 506 may be placed over the free posts of the pedicle screws 508 and glided into position along the pedicle screws. When a minimally invasive approach is used with a small access port for each individual pedicle screw, the bone graft implant 500 may be inserted into the patients body through one aperture, with the placement of a grommet 506 over the post of the pedicle screw, and then threaded under the patient's skin up to the next pedicle screw for placement of the next grommet, and so forth for the number of pedicle screws that are being utilized. A string may be threaded between the adjacent pedicle screws to aid in the pulling of the bone graft implant 500 between the access ports.

The various spinal fixation or instrumentation systems described herein as exemplary embodiments of the invention may be utilized in the performance of spinal fusion procedures using a streamlined method that is intended to simplify and shorten conventional spinal fusion procedures. Prior to operating, imaging of the patient may be utilized to determine the number of pedicle screws that will be linked together as part of the spinal fusion procedure. Further, an image guidance system may be utilized as part of the procedure to aid in the placement of the various components. In the case of an open procedure, an entry site is created in the patient along the portion of the spine into which the pedicle screws will be inserted. In the case of a minimally invasive procedure, individual entry ports may be utilized for implantation of individual pedicle screws. The various embodiments of the invention described herein are particularly suited to a minimally invasive approach because the coupling components are placed upon the screw from the top, allowing insertion and connection of the components via the small percutaneous aperture created for the screw itself in contrast to other designs requiring the use of coupling components that are not in line with the longitudinal axis of the screw, which may require an open procedure.

After creating the entry site and determining the point of insertion of a pedicle screw, the pedicle screws described herein that are self drilling may be drilled directly through the pedicles and into the vertebra. Alternatively, if the drill system described herein is utilized, the drill may be inserted into the pedicle screw, using the holding device to hold the drill in place, and utilized to drill into the pedicle simultaneously with the pedicle screw. Alternatively, conventional procedures may be utilized, including the pre-drilling and tapping of a hole in the pedicle, utilizing a Kirschner wire or guide wire as appropriate. The cannulated pedicle screws described herein are useful for incorporating the drill or for the use of a guide wire as desired by the surgeon.

After installation of the desired number of pedicle screws, the coupling mechanism is then utilized to connect the pedicle screws to a linking device, such as a fixation rod or plate as shown and described herein with respect to several exemplary embodiments. In the case of a minimally invasive procedure, multiple drills may be utilized to aid in the installation of the coupling components and the linking device may be threaded beneath the patient's skin between the various pedicle screws that are being linked to each other.

After the pedicle screws have been placed into the vertebrae, the transverse processes are decorticated prior to placing a bone graft material to aid in the fusion of the adjacent vertebrae. Implantation of the bone graft material is typically done prior to the insertion of the fixation rod or plate to attach the pedicle screws together. The bone graft implant shown in one embodiment in FIGS. 26 and 27 may be utilized to insert the bone graft material. If a drill, such as drill 414, is utilized during the process of attaching the pedicle screws to the spine, the coupling components may be placed on to the shaft of the drill to aid in the attachment of the fixation rod or plate. The drills that are utilized may then be removed from the pedicle screws. The installation of all the components may be aided by a guidance system such as a fluoronavigation system, especially in the case of minimally invasive procedures requiring image guidance where visual access is obscured.

While the detailed drawings and specific examples given herein describe various exemplary embodiments, they serve the purpose of illustration only. It is to be understood that the invention is not limited in its application to the details of construction and arrangements of components set forth in the preceding description or illustrated in the drawings. It should be noted that the components and/or assemblies of the spinal fixation systems may be constructed from various materials known in the art. Further, while several examples show the invention in the context of pedicle screw embodiments, the invention is also applicable to other surgical procedures involving a bone anchoring element or bone screw. Further, the order of performance of the method steps described with respect to spinal fixation procedures utilizing the various embodiments of the present invention may vary. Furthermore, other substitutions, modifications, changes and omissions may be made in the design, operating conditions, and arrangements of the exemplary embodiments without departing from the scope of the invention as expressed in the appended claims.

What is claimed is:

1. A spinal fixation system comprising:
a first pedicle screw having a longitudinal axis;
a passage in the first pedicle screw extending along the longitudinal axis, the passage having a proximal opening at a proximal end of the first pedicle screw and a distal opening at a distal end of the first pedicle screw;
a first drill extending through the passage in the first pedicle screw, a first end of the first drill extending out of the distal opening of the passage, wherein the first end has a pointed tip and cutting edges for boring into bone;
a holding device adapted to be placed over the first drill and removably coupled to the first pedicle screw, wherein a second end of the first drill extends from the holding device;
wherein the passage in the first pedicle screw comprises a keyed portion and the first drill comprises a keyed segment, the keyed segment and the keyed portion configured to interlock with one another wherein rotation of the first drill results in a corresponding rotation of the first pedicle screw;
a second drill;
a second first pedicle screw having a second longitudinal passage configured to receive the second drill;
a linking device configured to connect the first pedicle screw to the second first pedicle screw; and
a coupling mechanism adapted to couple the linking device to the first pedicle screw, wherein the coupling mechanism comprises at least one annular component sized to be fitted over the first pedicle screw and the first drill.

2. The spinal fixation system of claim 1, wherein a second end of the first drill extends out the proximal opening of the passage.

3. The spinal fixation system of claim 1, wherein the holding device is tubular.

4. The spinal fixation system of claim 3, wherein the holding device has a plurality of prongs and the pedicle screw has a flange and wherein the prongs snap onto the flange to couple the holding device to the pedicle screw.

5. The spinal fixation system of claim 1, wherein the linking device is a fixation plate.

6. A spinal fixation system comprising:
a first pedicle screw having a longitudinal axis;
a passage in the first pedicle screw extending along the longitudinal axis, the passage having a proximal opening at a proximal end of the first pedicle screw and a distal opening at a distal end of the first pedicle screw;
a first drill extending through the passage in the first pedicle screw, a first end of the first drill extending out of the distal opening of the passage, wherein the first end has a pointed tip and cutting edges for boring into bone;

wherein the passage in the first pedicle screw comprises a keyed portion and the first drill comprises a keyed segment, the keyed segment and the keyed portion configured to interlock with one another wherein rotation of the first drill results in a corresponding rotation of the first pedicle screw;

a second drill;

a second pedicle screw having a longitudinal passage configured to receive the second drill;

a linking device configured to connect the first pedicle screw to the second pedicle screw; and a coupling mechanism adapted to couple the linking device to the first pedicle screw, wherein the coupling mechanism comprises at least one annular component sized to be fitted over the first pedicle screw and the first drill, wherein the at least one component is a collet configured to be secured to the first pedicle screw.

7. A spinal fixation system comprising:

a pedicle screw having a longitudinal axis;

a passage in the pedicle screw extending along the longitudinal axis, the passage having a proximal opening at a proximal end of the pedicle screw and a distal opening at a distal end of the pedicle screw;

a drill extending through the passage in the pedicle screw, a first end of the drill extending out the distal opening of the passage, wherein the first end has a drill tip;

a linking device configured to connect the pedicle screw to at least one additional pedicle screw; and a coupling mechanism configured to be received on the pedicle screw, the coupling mechanism comprising:
 a collet having a plurality of compressible arms configured to engage the pedicle screw, wherein each compressible arm has an inner surface and an outer surface;
 a collar having an inner surface and an outer surface, wherein, when assembled, the inner surface of the collar directly contacts the outer surfaces of the compressible arms of the collet and the inner surfaces of the compressible arms directly contact the pedicle screw; and
 a fastening device, the fastening device coupling both the linking device and the collet to the pedicle screw.

8. The spinal fixation system of claim 7, wherein the passage comprises a keyed portion and further comprising a driver comprising a keyed segment, the keyed segment and the keyed portion configured to interlock with one another wherein rotation of the driver results in a corresponding rotation of the pedicle screw.

9. The spinal fixation system of claim 7, wherein the linking device is a fixation plate.

10. A spinal instrumentation kit comprising:

a first pedicle screw having a passage extending along a longitudinal axis of the first pedicle screw, the passage having a proximal opening at a proximal end of the first pedicle screw and a distal opening at a distal end of the first pedicle screw;

a first drill adapted to extend through the passage;

a holding device adapted to be placed over the first drill and removably coupled to the first pedicle screw, the holding device having a passage;

wherein the first drill is longer than the passage of the first pedicle screw and the passage of the holding device whereby a first end of the first drill is adapted to extend out the proximal opening of the first pedicle screw passage and a second end of the first drill is adapted to extend out of the holding device passage, wherein the first end of the first drill has a pointed tip and cutting edges for boring into bone;

wherein the passage comprises a keyed portion and the first drill comprises a keyed segment, the keyed segment and the keyed portion configured to interlock with one another wherein rotation of the first drill results in a corresponding rotation of the first pedicle screw;

a second drill;

a second pedicle screw having a second longitudinal passage configured to receive the second drill;

a linking device configured to connect the first pedicle screw to the second pedicle screw; and a coupling mechanism adapted to couple the linking device to the first pedicle screw, wherein the coupling mechanism comprises at least one annular component sized to be fitted over the first pedicle screw and the first drill.

11. The spinal instrumentation kit of claim 10, wherein the holding device is tubular.

12. The spinal instrumentation kit of claim 10, wherein the linking device is a fixation plate.

13. The spinal instrumentation kit of claim 10, wherein the drill comprises an expanded segment, wherein the keyed segment of the drill is located between the pointed tip and the expanded segment, and wherein the expanded segment of the drill has a diameter that is larger than a diameter of the drill at the pointed tip and is substantially the same as a diameter of the proximal end of the pedicle screw.

14. A spinal instrumentation kit comprising:

a first pedicle screw having a passage extending along a longitudinal axis of the first pedicle screw, the passage having a proximal opening at a proximal end of the first pedicle screw and a distal opening at a distal end of the first pedicle screw;

a first drill adapted to extend through the passage;

wherein the first drill is longer than the passage whereby an end of the first drill is adapted to extend out the proximal opening of the first pedicle screw passage, wherein the end of the first drill has a pointed tip and cutting edges for boring into bone;

wherein the passage comprises a keyed portion and the first drill comprises a keyed segment, the keyed segment and the keyed portion configured to interlock with one another, wherein rotation of the first drill results in a corresponding rotation of the first pedicle screw;

a second drill;

a second pedicle screw having a second longitudinal passage configured to receive the second drill;

a linking device configured to connect the first pedicle screw to the second pedicle screw;

a coupling mechanism adapted to couple the linking device to the first pedicle screw, wherein the coupling mechanism comprises at least one annular component sized to be fitted over the first pedicle screw and the first drill, wherein the at least one component is a collet configured to be secured to the first pedicle screw.

15. A spinal fixation system comprising:

a pedicle screw having a longitudinal axis and a passage extending along the longitudinal axis, the passage having a proximal opening at a proximal end of the pedicle screw and a distal opening at a distal end of the pedicle screw;

a drill extending through the passage in the pedicle screw and having a first end, the first extending out the distal opening of the passage and having a drill tip;

a linking device connecting the pedicle screw to at least one additional pedicle screw; and a coupling mechanism received on the pedicle screw and comprising:
- a collet having a plurality of compressible arms configured to engage the pedicle screw, each compressible arm having an inner surface and an outer surface;
- a collar having an inner surface and an outer surface, wherein, when assembled, the collet is located at least partially within the collar so that the inner surface of the collar directly contacts the outer surfaces of the compressible arms of the collet and the inner surfaces of the compressible arms directly contact the pedicle screw; and
- a fastening device coupling both the linking device and the collet to the pedicle screw.

* * * * *

UNITED STATES PATENT AND TRADEMARK OFFICE
CERTIFICATE OF CORRECTION

| | | |
|---|---|---|
| PATENT NO. | : 7,938,848 B2 | Page 1 of 1 |
| APPLICATION NO. | : 10/864673 | |
| DATED | : May 10, 2011 | |
| INVENTOR(S) | : Patrick J. Sweeney | |

It is certified that error appears in the above-identified patent and that said Letters Patent is hereby corrected as shown below:

IN THE CLAIMS

Claim 1:
Column 12, line 41, replace "a second first pedicle screw" with -- a second pedicle screw --.

Signed and Sealed this
Fifth Day of July, 2011

David J. Kappos
*Director of the United States Patent and Trademark Office*